(12) United States Patent
Okawa

(10) Patent No.: US 8,686,174 B2
(45) Date of Patent: Apr. 1, 2014

(54) PARTIALLY HYDROCARBON GROUP-BLOCKED (POLY)GLYCEROL-MODIFIED POLYSILOXANE, METHOD FOR PRODUCING THE SAME, AND COSMETIC COMPOSITION CONTAINING THE SAME

(75) Inventor: Tadashi Okawa, Ichihara (JP)

(73) Assignee: Dow Corning Toray Co. Ltd., Chiyoda-Ku, Tokyo (JP)

( * ) Notice: Subject to any disclaimer, the term of this patent is extended or adjusted under 35 U.S.C. 154(b) by 234 days.

(21) Appl. No.: 13/140,560

(22) PCT Filed: Dec. 21, 2009

(86) PCT No.: PCT/JP2009/071830
§ 371 (c)(1),
(2), (4) Date: Jun. 17, 2011

(87) PCT Pub. No.: WO2010/074296
PCT Pub. Date: Jul. 1, 2010

(65) Prior Publication Data
US 2011/0251417 A1    Oct. 13, 2011

(30) Foreign Application Priority Data

Dec. 22, 2008 (JP) ................................ 2008-326576

(51) Int. Cl.
*C07F 7/18* (2006.01)
(52) U.S. Cl.
USPC ................................ 556/425; 556/9; 528/31
(58) Field of Classification Search
USPC ....................................... 528/31; 556/9, 425
See application file for complete search history.

(56) References Cited

U.S. PATENT DOCUMENTS

| | | | |
|---|---|---|---|
| 4,431,789 A | 2/1984 | Okazaki et al. | |
| 4,520,160 A | 5/1985 | Brown | |
| 4,816,506 A | 3/1989 | Gamon et al. | |
| 5,763,505 A | 6/1998 | Derian et al. | |
| 6,221,934 B1 | 4/2001 | Stark et al. | |
| 6,710,092 B2 | 3/2004 | Scher et al. | |
| 6,995,210 B2 | 2/2006 | Bouvy et al. | |
| 8,034,891 B2 * | 10/2011 | Okawa | 528/31 |
| 2002/0131947 A1 | 9/2002 | Nakanishi | |
| 2003/0105169 A1 | 6/2003 | Lennon | |
| 2005/0008600 A1 | 1/2005 | Nakanishi et al. | |
| 2005/0089697 A1 | 4/2005 | Benayoun et al. | |
| 2007/0238829 A1 | 10/2007 | Paul | |
| 2010/0036062 A1 | 2/2010 | Okawa | |
| 2011/0251417 A1 | 10/2011 | Okawa | |

FOREIGN PATENT DOCUMENTS

| | | |
|---|---|---|
| CN | 1441822 A | 9/2003 |
| CN | 101080440 A | 11/2007 |
| CN | 101084870 A | 12/2007 |
| EP | 0266729 A2 | 5/1988 |
| EP | 1055771 A1 | 11/2000 |
| EP | 2022812 A1 | 2/2009 |
| JP | 57149290 A | 9/1982 |
| JP | S60-156733 A | 8/1985 |
| JP | 61212321 | 9/1986 |
| JP | H02-265926 A | 10/1990 |
| JP | 06145524 | 5/1994 |
| JP | 06-234858 A | 8/1994 |
| JP | 06234918 | 8/1994 |
| JP | 07133354 | 5/1995 |
| JP | 10-176059 A | 6/1998 |
| JP | 10-279688 A | 10/1998 |
| JP | 11148010 | 6/1999 |
| JP | 11148011 | 6/1999 |
| JP | 2000086437 | 3/2000 |
| JP | 2001294666 | 10/2001 |
| JP | 2004339244 | 12/2004 |
| JP | 2005089494 | 4/2005 |
| JP | 2010-144156 A | 7/2010 |
| WO | WO 2007135771 A1 | 11/2007 |
| WO | WO 2010074295 A1 | 7/2010 |
| WO | WO 2010074297 A1 | 7/2010 |

OTHER PUBLICATIONS

English language abstract for EP 0266729 extracted from the espacenet.com database on Jul. 28, 2011, 9 pages.
English language abstract and translation for JP 06145524 extracted from the PAJ database on Jul. 26, 2011, 28 pages.
English language abstract and translation for JP 06234918 extracted from the PAJ database on Jul. 26, 2011, 30 pages.
English language abstract and translation for JP 07133354 extracted from the PAJ database on Jul. 26, 2011, 31 pages.
English language abstract and translation for JP 11148010 extracted from the PAJ database on Jul. 26, 2011, 40 pages.

(Continued)

*Primary Examiner* — Johann R Richter
*Assistant Examiner* — Pancham Bakshi
(74) *Attorney, Agent, or Firm* — Howard & Howard Attorneys PLLC

(57) ABSTRACT

The present invention provides a novel modified-polysiloxane, method for producing the same, and a cosmetic containing the same. The aforementioned modified-polysiloxane exhibits a reduced viscosity and superior operationability as compared with conventional polyoxyalkylene-modified polysiloxanes and polyglycerol-modified polysiloxanes. In addition, since the modified-polysiloxane is hardly oxidized in air, hardly produce allergenic compounds such as formates, and aldehydes such as formaldehyde, during storage over time, an increased environmental compatibility can be exhibited. In addition, the modified-polysiloxane of the present invention exhibits a reduced hydrolysis property and is stable. In the modified-polysiloxane of the present invention, the terminal hydroxyl groups of a polyglycerol-modified polysiloxane are partially blocked with hydrocarbon groups.

11 Claims, 6 Drawing Sheets

(56) References Cited

OTHER PUBLICATIONS

English language abstract and translation for JP 11148011 extracted from the PAJ database on Jul. 28, 2011, 33 pages.
English language abstract for JP 57149290 extracted from the espacenet.com database on Jul. 28, 2011, 12 pages.
English language abstract for JP 61212321 extracted from the PAJ database on Jul. 26, 2011, 11 pages.
English language abstract and translation for JP 2000086437 extracted from the PAJ database on Jul. 26, 2011, 30 pages.
English language abstract and translation for JP 2001294666 extracted from the PAJ database on Jul. 28, 2011, 37 pages.
English language abstract and translation for JP 2004339244 extracted from the PAJ database on Jul. 28, 2011, 140 pages.
English language abstract and translation for JP 2005089494 extracted from the PAJ database on Jul. 28, 2011, 47 pages.
English language abstract for JP 2010144156 extracted from the espacenet.com database on Jul. 28, 2011, 107 pages.
English language abstract for WO 2007135771 extracted from the espacenet.com database on Jul. 28, 2011, 159 pages.
International Search Report for Application No. PCT/JP2009/071830 dated Dec. 21, 2009, 3 pages.
International Search Report for Application No. PCT/JP2009/071831 dated Dec. 21, 2009, 3 pages.
International Search Report for Application No. PCT/JP2009/071829 dated Dec. 21, 2009, 3 pages.
English language abstract not available for CN 1441822; however, see English language equivalent US 6,995,210. Orginal Document extracted from the espacenet.com database on Oct. 5, 2012, 35 pages.
English language abstract not available for CN 101080440; however, see English language equivalent US 2007/0238829. Original Document extracted from the espacenet.com database on Oct. 5, 2012, 26 pages.
English language abstract for CN 101084870 extracted from the espacenet.com database on Oct. 5, 2012, 12 pages.
English language abstract for JP 2010-144156 extracted from the espacenet.com database on Oct. 5, 2012, 43 pages.
Margareta Bergh et al., "Formation of formaldehyde and peroxides by air oxidation of high purity polyoxyethylene surfactants." Contact Dermatitis, 39, 14-20 (1998).
Margareta Bergh et al., "Contact Allergens from Surfactants. Atmospheric Oxidation of Polyoxyethylene Alcohols, Formation of Ethoxylated Aldehydes, and Their Allergenic Activity." Journal of Pharmaceutical Sciences, 87, 276-282 (1998).
International Search Report for Application No. PCT/JP2009/071830 dated Feb. 19, 2010, 3 pages.
International Search Report for Application No. PCT/JP2009/071831 dated Apr. 20, 2010, 3 pages.
International Search Report for Application No. PCT/JP2009/071829 dated Jun. 16, 2010, 3 pages.
Margareta Bergh et al., "Atmospheric Oxidation of Poly(oxyethylene) Alcohols. Identification of Ethoxylated Formates as Oxidation Products and Study of Their Contact Allergenic Activity." Journal of Pharmaceutical Sciences, 88, 4 (1999).
Margareta Bergh et al., "Formation of formaldehyde and peroxides by air oxidation of high purity polyoxyethylene surfactants." Contact Dermatitis, 39, 14 (1998).
Anna Bodin et al., "Identification and allergenic activity of hydroxyaldehydes—a new type of oxidation product from an ethoxylated non-ionic surfactant." Contact Dermatitis, 44, 207-212 (2001).
Margareta Bergh et al., "Contact Allergens from Surfactants. Atmospheric Oxidation of Polyoxyethylene Alcohols, Formation of Ethoxylated Aldehydes, and Their Allergenic Activity." Journal of Pharmaceutical Sciences, 87, 276 (1998).
Margareta Bergh et al., "Allergenic Oxidation Products in Ethoxylated Non-Ionic Surfactants." Acta Dermato-Venereologica, 79, 5-26 (1999).
Margareta Bergh et al., "Atmospheric Oxidation of Poly(oxyethylene) Alcohols. Identification of Ethoxylated Formates as Oxidation Products and Study of Their Contact Allergenic Activity." Journal of Pharmaceutical Sciences, 88, 4, 483-488, (1999).
English language abstract for JP H02-265926 extracted from the espacenet.com database on Sep. 18, 2013, 17 pages.
English language abstract and machine-assisted English translation for JP 06-234858 extracted from the PAJ database on Sep. 18, 2013, 58 pages.
English language abstract and machine-assisted English translation for JP 10-176059 extracted from the PAJ database on Sep. 18, 2013, 38 pages.
English language abstract and machine-assisted English translation for JP 10-279688 extracted from the PAJ database on Oct. 20, 1998, 88 pages.
English language abstract not available for JP S60-156733; however, see English equivalent US 4,520,160. Original Document extracted from the espacenet.com database on Sep. 18, 2013, 7 pages.

* cited by examiner

PARTIALLY HYDROCARBON GROUP-BLOCKED (POLY)GLYCEROL-MODIFIED POLYSILOXANE, METHOD FOR PRODUCING THE SAME, AND COSMETIC COMPOSITION CONTAINING THE SAME

RELATED APPLICATIONS

This application claims priority to and all the advantages of International Patent Application No. PCT/JP2009/071830, filed on Dec. 21, 2009, which claims priority to Japanese Patent Application No. JP 2008-326576, filed on Dec. 22, 2008.

TECHNICAL FIELD

The present invention relates to a novel partially hydrocarbon group-blocked (poly)glycerol-modified polysiloxane, in which a polysiloxane is modified with a polyglycerol of which one or more terminal hydroxyl groups are blocked with hydrocarbon groups, and a method for producing the same, as well as a cosmetic containing the aforementioned partially hydrocarbon group-blocked (poly)glycerol-modified polysiloxane.

Priority is claimed on Japanese Patent Application No. 2008-326576, filed on Dec. 22, 2008, the content of which is incorporated herein by reference.

BACKGROUND ART

Heretofore, a polyglycerol-modified polysiloxane in which an organopolysiloxane is modified with a polyglycerol is known, and is used, for example, as a component of a cosmetic.

Japanese Unexamined Patent Application, First Publication No. S57-149290 discloses a method for producing a polyglycerol-modified polysiloxane in which a terminal-alkenyl polyglycerol obtained by subjecting glycidol to a ring opening polymerization with an alkenyl alcohol as an initiator in the presence of an alkali hydroxide catalyst is addition-reacted with a polyorganohydrogensiloxane.

Japanese Unexamined Patent Application, First Publication No. 2005-089494 discloses a method for producing a polyglycerol-modified polysiloxane by subjecting an alkenyl-terminal branched polyglycerol to an addition reaction with a polyorganohydrogensiloxane, which is basically the same preparation method as described in Japanese Unexamined Patent Application, First Publication No. S57-149290. In the preparation method described in Japanese Unexamined Patent Application, First Publication No. 2005-089494, it is demonstrated that the branched polyglycerol-modified polysiloxane can be obtained by a $^{13}$C NMR chart. On the other hand, Japanese Unexamined Patent Application, First Publication No. S57-149290 describes that a linear polyglycerol-modified polysiloxane is obtained by basically the same preparation method as described above. Japanese Unexamined Patent Application, First Publication No. S57-149290 fails to attach a $^{13}$C NMR analysis chart, and for this reason, it is believed that a branched polyglycerol-modified polysiloxane might be practically obtained in accordance with the preparation method of the aforementioned patent document.

On the other hand, Japanese Unexamined Patent Application, First Publication No. 2004-339244 discloses a branched polyglycerol-modified polysiloxane obtained by subjecting glycidol to a ring opening polymerization in the presence of an alkali hydroxide catalyst using an active hydrogen group-containing organopolysiloxane as a polymerization initiator, and a method for producing the same.

However, in the preparation method described in Japanese Unexamined Patent Application, First Publication No. 2004-339244, a bindscission reaction of a siloxane bond due to a growing alcholate anion occurs as a side reaction, and thereby, not only a polymer having a chemical structure estimated from a charging ratio cannot be obtained, but also the obtained branched polyglycerol-modified polysiloxane contains a large amount of an Si—O—C bond. For these reasons, there are problems in that hydrolysis reactivity is increased, and quality of the product per se or an aqueous solution thereof is deteriorated over time.

In addition, in the polyglycerol-modified polysiloxanes obtained by the aforementioned preparation methods, the degree of polymerization of polyglycerol is increased. In the case of having a high content rate thereof, an extremely high viscosity is exhibited, and operation ability is impaired. Therefore, a polyglycerol-modified polysiloxane derivative having a reduced viscosity and exhibiting better operation ability, as compared with a polyglycerol-modified polysiloxane, has been desirable.

On the other hand, a polyether-modified polysiloxane in which an organopolysiloxane is modified by a polyether is also known, and for example, is commonly used as a component of a cosmetic. It is reported that a polyether-modified polysiloxane is easily oxidized in air, and carbonyl-functional allergenic compounds such as formates and aldehydes such as formaldehyde are produced during storage over time in *Acta Dermato-Venereologica*, 79, 5-26 (1999); *J Pharm Sci*, 87, 276 (1998); *Contact Dermatitis*, 44, 207 (2001); *Contact Dermatitis*, 39, 14 (1998); *J Pharm Sci*, 88, 4 (1999); *Contact Dermatitis*, 44, 207-212, 2001; and the like.

[Patent Document 1] Japanese Unexamined Patent Application, First Publication No. S57-149290
[Patent Document 2] Japanese Unexamined Patent Application, First Publication No. 2005-089494
[Patent Document 3] Japanese Unexamined Patent Application, First Publication No. 2004-339244
[Non-Patent Document 1] *Acta Dermato-Venereologica*, 79, 5-26 (1999)
[Non-Patent Document 2] *J Pharm Sci*, 87, 276 (1998)
[Non-Patent Document 3] *Contact Dermatitis*, 44, 207 (2001)
[Non-Patent Document 4] *Contact Dermatitis*, 39, 14 (1998)
[Non-Patent Document 5] *J Pharm Sci*, 88, 4 (1999)
[Non-Patent Document 6] *Contact Dermatitis*, 44, 207-212, 2001

DISCLOSURE OF THE INVENTION

Problems to be Solved by the Invention

An objective of the present invention is to provide a novel modified polysiloxane with reduced viscosity providing superior operation ability, as compared with a conventional polyglycerol-modified polysiloxane, which is difficult to be oxidized as compared with, a conventional polyether-modified polysiloxane and therefore, it has increased environmental compatibility as it is difficult to produce allergenic compounds such as formates and aldehydes such as formaldehyde over time during storage. Further, the present invention is to provide a cosmetic containing the aforementioned novel modified polysiloxane. Furthermore, the present invention is to provide a method for producing a novel modified polysiloxane in which hydrolysis decomposition properties of products are reduced, and stability is exhibited, as compared with a conventional method for producing a polyglycerol-modified polysiloxane.

Means for Solving the Problems

The objective of the present invention can be achieved by a partially hydrocarbon group-blocked (poly)glycerol-modified polysiloxane in which at least one terminal group represented by the following formula (1), (2), or (3):

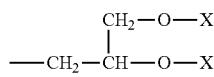  (1)

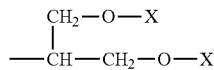  (2)

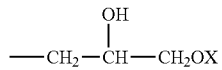  (3)

wherein X represents a hydrogen atom or independently represents a substituted or non-substituted monovalent hydrocarbon group containing no aliphatic unsaturated bond, with not more than 20 carbon atoms; and at least one of the Xs is the aforementioned hydrocarbon group,
binds to a silicon atom of an organopolysiloxane via a linking group. At least 15% of the Xs of the aforementioned terminal groups is preferably the aforementioned hydrocarbon group.

The aforementioned linking group preferably contains a divalent group represented by the following general formula (4):

$$-R^1-O-(AO)_p-$$  (4)

wherein
$R^1$ represents a substituted or non-substituted, linear or branched alkylene group having 1 to 22 carbon atoms, or a substituted or non-substituted alkylenearylene group having 6 to 22 carbon atoms;
AO independently represents an alkyleneoxy group having 1 to 4 carbon atoms, or an aryleneoxy group having 6 to 10 carbon atoms; and
p represents a number ranging from 0 to 30; with the proviso that $R^1$ binds to a silicon atom,
or a divalent group represented by the following general formula (5):

$$-R^1-COO-(AO)_p-$$  (5)

wherein
$R^1$, AO and p are the same as described above.
The aforementioned linking group preferably further contains at least one moiety represented by the following formula (6), (7), (8) or (9):

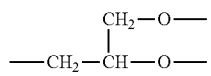  (6)

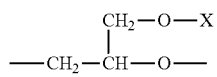  (7)

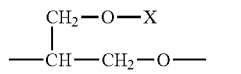  (8)

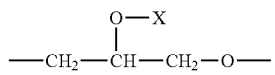  (9)

wherein X is the same as described above. The aforementioned moiety can be present in an amount ranging from 1 to 500 moieties in the aforementioned linking group.

The aforementioned partially hydrocarbon group-blocked (poly)glycerol-modified polysiloxane can be represented by the following average unit formula (10):

$$R^2_a(R^3)_b SiO_{(4-a-b)/2}$$  (10)

wherein
$R^2$ represents a substituted or non-substituted monovalent hydrocarbon group containing no aliphatic unsaturated bond; $R^3$ represents a partially hydrocarbon group-blocked (poly)glycerol-modified group represented by $-R^4-R^5$, wherein $R^4$ represents the aforementioned linking group; and $R^5$ represents the aforementioned terminal group; and $1.0 \leq a \leq 2.5$, and $0.001 \leq b \leq 1.5$.

The aforementioned partially hydrocarbon group-blocked (poly)glycerol-modified polysiloxane can be produced by reacting an organohydrogenpolysiloxane and a partially hydrocarbon group-blocked (poly)glycerol in which at least one terminal group represented by the following formula (1), (2) or (3):

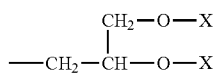  (1)

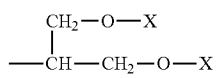  (2)

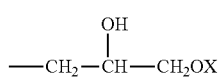  (3)

in each of the formulae, X represents a hydrogen atom or independently represents a substituted or non-substituted monovalent hydrocarbon group containing no aliphatic unsaturated bond, with not more than 20 carbon atoms; and at least one of the Xs is the aforementioned hydrocarbon group, binds to an aliphatic unsaturated hydrocarbon group of an organopolysiloxane via a linking group,
in the presence of an addition reaction catalyst. At least 15% of the Xs of the aforementioned terminal groups is preferably the aforementioned hydrocarbon group.

The aforementioned linking group preferably contains a divalent group represented by the following general formula (4'):

$$-R^6-O-(AO)_p-$$  (4')

wherein
$R^6$ represents a substituted or non-substituted, linear or branched alkylene group having 1 to 20 carbon atoms, or a substituted or non-substituted alkylenearylene group having 6 to 20 carbon atoms;
AO independently represents an alkyleneoxy group having 1 to 4 carbon atoms, or an aryleneoxy group having 6 to 10 carbon atoms; and p represents a number ranging from 0 to 30; with the proviso that $R^6$ binds to the aliphatic unsaturated hydrocarbon group, or a divalent group represented by the following general formula (5'):

$$—R^6—COO-(AO)_p— \quad (5')$$

wherein
$R^6$, AO, and p are the same as described above.

The aforementioned linking group preferably further contains at least one moiety represented by the following formula (6), (7), (8) or (9):

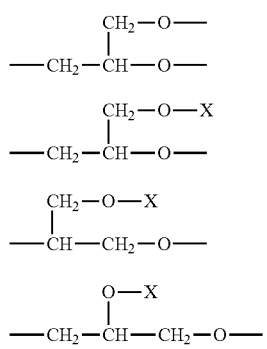

wherein X is the same as described above.

As the aforementioned organohydrogenpolysiloxane, one represented by the following average unit formula (11):

$$R^2{}_a H_b SiO_{(4-a-b)/2} \quad (11)$$

wherein
$R^2$ represents a substituted or non-substituted monovalent hydrocarbon group containing no aliphatic unsaturated bond; and
$1.0 \leq a \leq 2.5$, and $0.001 \leq b \leq 1.5$,
is preferable.

The aforementioned aliphatic unsaturated hydrocarbon group is preferably a vinyl group or an allyl group.

The partially hydrocarbon group-blocked (poly)glycerol-modified polysiloxane of the present invention can be used as a component of a cosmetic, and is suitably blended in a cosmetic.

Effects of the Invention

The partially hydrocarbon group-blocked (poly)glycerol-modified polysiloxane of the present invention, in which terminal OH groups are partially alkylated, is different from a conventional polyglycerol-modified polysiloxane, and for this reason, hydrogen bonding between the aforementioned OH groups can be controlled. Therefore, the partially hydrocarbon group-blocked (poly)glycerol-modified polysiloxane of the present invention has reduced viscosity and exhibits superior operation properties, as compared with a conventional polyglycerol-modified polysiloxane. Therefore, the polysiloxane of the present invention is easily blended in a cosmetic or the like.

In addition, the partially hydrocarbon group-blocked (poly)glycerol-modified polysiloxane of the present invention is difficult to be oxidized in air, and allergenic compounds such as formates, aldehydes such as formaldehydes have difficulty being produced over time during storage, as compared with a conventional polyether-modified polysiloxane. For this reason, the polysiloxane of the present invention exhibits increased environmental compatibility even if an after-treatment such as a hydrogenation treatment or the like is not carried out. Therefore, the polysiloxane of the present invention can be used as a replacement of an existing polyether-modified polysiloxane.

As described above, the partially hydrocarbon group-blocked (poly)glycerol-modified polysiloxane of the present invention can be suitably used in a cosmetic or the like, which is used on human beings as an emulsifier without environmental pollution, since aldehydes which are harmful for human beings do not generate for a long period of time.

In addition, in the preparation method of the present invention, a partially hydrocarbon group-blocked (poly)glycerol-modified polysiloxane is synthesized in accordance with a hydrosilylation reaction. For this reason, the (poly)glycerol-modified moiety strongly binds to a polysiloxane not by an Si—O—C bond, but by an Si—C bond. Therefore, the partially hydrocarbon group-blocked (poly)glycerol-modified polysiloxane obtained by the preparation method of the present invention exhibits reduced hydrolysis decomposition properties, is stable over time, and can maintain the aforementioned properties thereof for a long time, as compared with a conventional polyglycerol-modified polysiloxane.

In a cosmetic in which the partially hydrocarbon group-blocked (poly)glycerol-modified polysiloxane of the present invention is present, allergenic compounds such as formaldehyde and the like do not generate during storage. For this reason, the cosmetic can be safely used for a long time. In addition, it is not necessary to add an antioxidant and the like in order to prevent generation of allergenic compounds. For this reason, a cosmetic having a more natural composition can be formed.

BEST MODES FOR CARRYING OUT THE INVENTION

Figure 1:
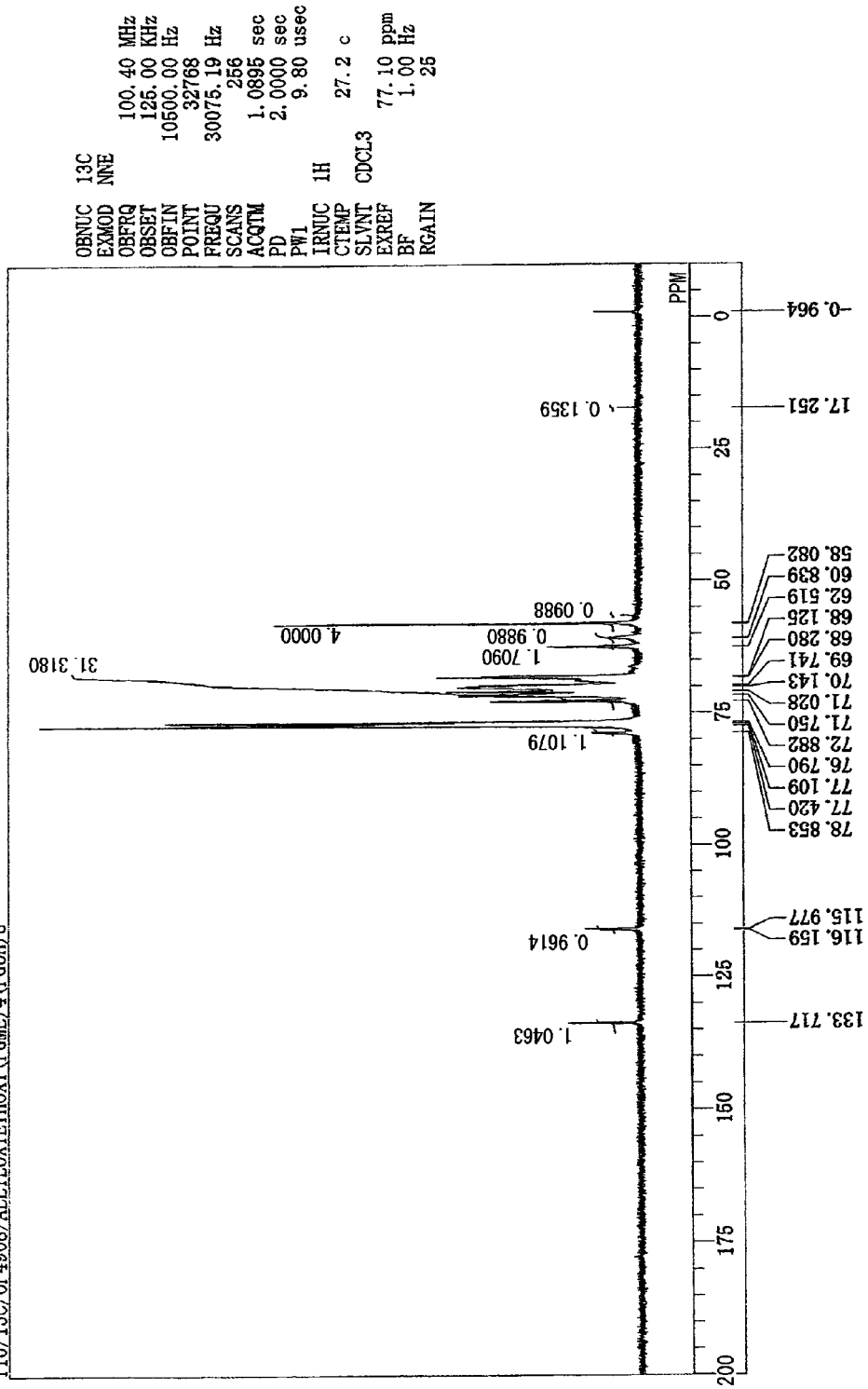
FIG. 1 is a $^{13}$C NMR chart of one terminal allyloxyethoxy group-blocked partially methylated polyglycerol produced in Example 1.

The partially hydrocarbon group-blocked (poly)glycerol-modified polysiloxane of the present invention has at least one terminal group represented by the following formula (1), (2), or (3):

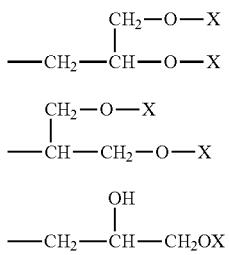

(1)

(2)

(3)

wherein X represents a hydrogen atom or independently represents a substituted or non-substituted monovalent hydrocarbon group containing no aliphatic unsaturated bond, with not more than 20 carbon atoms; and at least one of the Xs is the aforementioned hydrocarbon group.

As examples of the substituted or non-substituted monovalent hydrocarbon group containing no aliphatic unsaturated bond, with not more than 20 carbon atoms, mention may be made of, for example, saturated aliphatic hydrocarbon groups such as a methyl group, an ethyl group, a propyl group, a butyl group, a pentyl group, a hexyl group, a heptyl group, an octyl group, a decyl group, a dodecyl group, and the like; saturated alicyclic hydrocarbon groups such as a cyclopentyl group, a cyclohexyl group and the like; aromatic hydrocarbon groups such as a phenyl group, a tolyl group, a xylyl group, a naphthyl group and the like; and groups in which one or more hydrogen atoms bound to carbon atoms of the aforementioned groups are substituted with a halogen atom such as fluorine or the like, or an organic group containing an epoxy group, a glycidyl group, an acyl group, a carboxyl group, an amino group, a methacryl group, a mercapto group, or the like. A methyl group, an ethyl group or a phenyl group are, in particular, preferable.

In the terminal group of the partially hydrocarbon group-blocked (poly)glycerol-modified polysiloxane of the present invention, all of the Xs present therein are not OH groups, and at least one X and preferably not less than 15% thereof are blocked by a hydrocarbon group. For this reason; hydrogen bonding can be controlled. Therefore, the partially hydrocarbon group-blocked (poly)glycerol-modified polysiloxane has low viscosity, and superior operation properties are exhibited.

Preferably at least 20%, more preferably at least 30%, further more preferably at least 40%, furthermore preferably at least 50%, furthermore preferably at least 60% and further more preferably at least 70% of all the Xs present at the aforementioned terminal groups should be the aforementioned hydrocarbon group.

The aforementioned terminal group binds to a silicon atom of an organopolysiloxane via a linking group.

The aforementioned linking group preferably contains a divalent group represented by the following general formula (4):

wherein
$R^1$ represents a substituted or non-substituted, linear or branched alkylene group having 1 to 22 carbon atoms, or a substituted or non-substituted alkylenearylene group having 6 to 22 carbon atoms;
AO independently represents an alkyleneoxy group having 1 to 4 carbon atoms, or an aryleneoxy group having 6 to 10 carbon atoms; and
p represents a number ranging from 0 to 30; with the proviso that $R^1$ binds to a silicon atom, or a divalent group represented by the following general formula (5):

wherein
$R^1$, AO and p are the same as described above.

As examples of $R^1$, mention may be made of, for example, a dimethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, or dimethylenephenylene group, and the like. Among these, a dimethylene or trimethylene group is preferable. In view of easiness of synthesis, a trimethylene group is, in particular, preferable.

As examples of AO, mention may be made of, for example, an ethyleneoxy group, a propyleneoxy group, or a phenyleneoxy group. An ethyleneoxy group is preferable.

p may be a number ranging from 0 to 20, and preferably ranging from 0 to 10.

The aforementioned linking group preferably further contains at least one moiety represented by the following formula (6), (7), (8) or (9):

wherein X is the same as described above.

When the aforementioned moiety is present, the aforementioned moiety preferably directly binds to the aforementioned terminal group. More particularly, the direct binding is preferable so that the binding from the oxygen atom of anyone of the aforementioned formulae (6) to (9) corresponds to the binding from the carbon atom of the terminal group of the aforementioned formula (1), (2) or (3). The binding from the carbon atom of anyone of the aforementioned formulae (6) to (9) can correspond to the binding from the oxygen atom of any one of the aforementioned formulae (6) to (9), in the same manner as described above. In this case, plural moieties of any of the aforementioned formulae (6) to (9) are present in the aforementioned linking group, and one of the bindings from the moieties of the aforementioned formulae (6) to (9) binds to the oxygen atom of the divalent group of the aforementioned formula (4) or (5). The aforementioned moiety can be present in an amount ranging from 1 to 500, from 1 to 300, or from 1 to 200 in the aforementioned linking group.

In the aforementioned moiety, a small amount of an ethylene oxy group and/or a propyleneoxy group may be present. The aforementioned groups are unstable with respect to oxidation, and are easily decomposed to give a carbonyl-functional decomposed product. For this reason, the amount thereof is preferably not more than 0.5 molar equivalents with respect to 1 molar equivalent, and more preferably not more than 0.2 molar equivalents.

Therefore, the partially hydrocarbon group-blocked (poly)glycerol-modified polysiloxane of the present invention can be represented by the following average unit formula:

$$R^2{}_a(R^3)_b SiO_{(4-a-b)/2} \tag{10}$$

wherein
$R^2$ represents a substituted or non-substituted monovalent hydrocarbon group containing no aliphatic unsaturated bond; $R^3$ represents a partially hydrocarbon group-blocked (poly)glycerol-modified group represented by $-R^4-R^5$, wherein $R^4$ represents the aforementioned linking group; and $R^5$ represents the aforementioned terminal group; and
$1.0 \leq a \leq 2.5$, and $0.001 \leq b \leq 1.5$.

As examples of the aforementioned substituted or non-substituted monovalent hydrocarbon group containing no aliphatic unsaturated bond, those described above can be mentioned, and in particular, for example, an alkyl group such as a methyl group, an ethyl group, a propyl group or the like; an aryl group such as a phenyl group, a tolyl group, a xylyl group, an ethylphenyl group, or the like; or an aralkyl group such as a benzyl group, a phenethyl group or the like. In addition, as examples of the substituted or non-substituted monovalent hydrocarbon group containing no aliphatic unsaturated bond used here, mention may also be made of a fluorinated monovalent hydrocarbon group containing no aliphatic unsaturated bond or a polyoxyalkylene-substituted monovalent saturated hydrocarbon group.

As examples of the aforementioned fluorinated monovalent hydrocarbon group containing no aliphatic unsaturated bond, mention may be made of, for example, a trifluoromethyl group, a pentafluoroethyl group or the like. In addition, as examples of the aforementioned polyoxyalkylene-substituted monovalent saturated hydrocarbon group, mention may be made of, for example, a one-terminal hydroxyl group-blocked polyoxyalkylene-substituted monovalent alkyl group, or a one-terminal alkyl group-blocked polyoxyalkylene-substituted monovalent alkyl group. In particular, the following groups:

CH$_2$CH$_2$CH$_2$—O—(CH$_2$CH$_2$O)$_n$H

CH$_2$CH$_2$CH$_2$—O—(CH$_2$CH$_2$O)$_n$(CH$_2$CH(CH$_3$)O)$_m$H

CH$_2$CH$_2$CH$_2$—O—(CH$_2$CH$_2$O)$_n$CH$_3$

CH$_2$CH$_2$CH$_2$—O—(CH$_2$CH$_2$O)$_n$(CH$_2$CH(CH$_3$)O)$_m$CH$_3$ wherein each of n and m is an integer; and n<100 and n+m<100 are preferable.

The partially hydrocarbon group-blocked (poly)glycerol-modified polysiloxane of the present invention can be produced by reacting an organohydrogenpolysiloxane and a partially hydrocarbon group-blocked (poly)glycerol in which at least one terminal group represented by the following formula (1), (2) or (3):

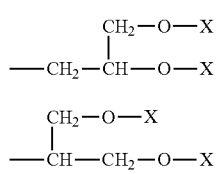

(1)

(2)

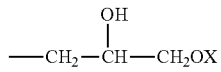

(3)

in each of the formulae, X represents a hydrogen atom or independently represents a substituted or non-substituted monovalent hydrocarbon group containing no aliphatic unsaturated bond, with not more than 20 carbon atoms; and at least one of the Xs is the aforementioned hydrocarbon group, binds to an aliphatic unsaturated hydrocarbon group via a linking group, in the presence of an addition reaction catalyst. At least 15% of the Xs of the aforementioned terminal groups are preferably the aforementioned hydrocarbon group.

The aforementioned linking group preferably contains a divalent group represented by the following general formula (4'):

$$-R^6-O-(AO)_p- \tag{4'}$$

wherein
$R^6$ represents a substituted or non-substituted, linear or branched alkylene group having 1 to 20 carbon atoms, or a substituted or non-substituted alkylenearylene group having 6 to 20 carbon atoms;
AO independently represents an alkyleneoxy group having 1 to 4 carbon atoms, or an aryleneoxy group having 6 to 10 carbon atoms; and
p represents a number ranging from 0 to 30; with the proviso that $R^6$ binds to the aliphatic unsaturated hydrocarbon group, or a divalent group represented by the following general formula (5'):

$$-R^6-COO-(AO)_p- \tag{5'}$$

wherein
$R^6$, AO, and p are the same as described above.

As examples of $R^6$, mention may be made of, for example, a methylene, dimethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, dimethylenephenylene group or the like. Among these, a methylene group, a dimethylene group or a trimethylene group is preferable, and in particular, a methylene group is preferable. Examples of AO, p and q are the same as described above.

As examples of the aliphatic unsaturated hydrocarbon group, mention may be made of a vinyl group, an allyl group, a butenyl group, a hexenyl group, an undecenyl group, or a vinylphenyl group. A vinyl group or an allyl group is preferable and a vinyl group is particularly preferable.

The aforementioned linking group preferably further contains at least one moiety represented by the following formula (6), (7), (8) or (9):

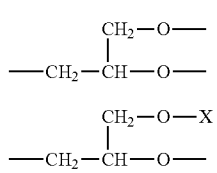

(6)

(7)

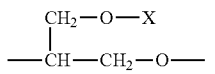

(8)

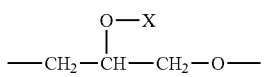

(9)

wherein X is the same as described above.

When the aforementioned moiety is present, the aforementioned moiety preferably directly binds to the aforementioned terminal group. More particularly, a direct binding is preferable so that the binding from the oxygen atom of any one of the aforementioned formulae (6) to (9) corresponds to the binding from the carbon atom of the terminal group of the aforementioned formula (1), (2) or (3). The binding from the carbon atom of any one of the aforementioned formulae (6) to (9) can correspond to the binding from the oxygen atom of any one of the aforementioned formulae (6) to (9), in the same manner as described above. In this case, plural moieties of any of the aforementioned formulae (6) to (9) are present in the aforementioned linking group. One of the bindings from the moieties of the aforementioned formulae (6) to (9) binds to the oxygen atom of the divalent group of the aforementioned formula (4') or (5'). The aforementioned moiety can be present in an amount ranging from 1 to 500, from 1 to 300, or from 1 to 200 in the aforementioned linking group.

The aforementioned partially hydrocarbon group-blocked (poly)glycerol can be obtained by, for example, subjecting glycidol, glycidyl ether obtained by replacing the hydrogen atom in the hydroxyl group of glycidol with the hydrocarbon group for forming the aforementioned X group, or a mixture of glycidol and glycidyl ether to a ring-opening (co)polymerization in the presence of an acid or basic catalyst using an aliphatic unsaturated bond-containing alcohol or carboxylic acid such as ethylene glycol monoallyl ether or the like as an initiator. The ring-opening (co)polymerization can be carried out in accordance with a conventional method. When a mixture of glycidyl ether and glycidol are copolymerized, one corresponding to a random copolymer can be obtained. On the other hand, when one is polymerized and then another is added to polymerize these, one corresponding to a block copolymer can be obtained. Two or more types of glycidyl ethers can also be used.

In addition, the aforementioned partially hydrocarbon group-blocked (poly)glycerol can also be produced by means of a so-called Williamson ether synthesis reaction, which comprises subjecting glycidol to a ring-opening polymerization in the presence of an acid or basic catalyst using the aforementioned aliphatic unsaturated bond-containing alcohol or carboxylic acid as an initiator, subsequently adding a specified amount of an alkali hydroxide to form an alkali-alcholated terminal of a molecular chain, and subsequently reacting with a halogenated hydrocarbon to partially replace hydrogen atoms in the hydroxyl groups with hydrocarbon groups.

As examples of the acid polymerization catalyst, mention may be made of Lewis acids such as $BF_3 \cdot OEt_2$, $HPF_6 \cdot OEt_2$, $TiCl_4$, $SnCl_4$, sulfuric acid, $PhCOSbF_6$, perchloric acid, fluorosulfuric acid, trifluoroacetic acid, trifluoromethanesulfonic acid and the like, wherein Et represents an ethyl group; and Ph represents a phenyl group. As examples of basic polymerization catalysts, mention may be made of a metal hydroxide such as LiOH, NaOH, KOH, CsOH or the like; an alkali metal such as Li, Na, K, Cs or the like or mercury amalgam thereof; a metal alcholate represented by the following general formula: $ROM^1$, wherein R=alkyl group, and preferably an alkyl group having 1 to 4 carbon atoms, and $M^1$=alkali metal; a metal hydride of which the metal is an alkali metal or an alkaline earth metal; an organometal compound such as n-butyl lithium, t-butyl lithium, potassium pentadienyl, potassium naphthalene, Grignard reagent or the like; and the like. Among these, the alkali metal, metal hydroxide, metal alcholate or organometal compound is preferable due to high activity. In particular, K, KOH, CsOH, potassium hydride, potassium methoxide, potassium isopropoxide, or potassium t-butoxide is particularly preferably as a catalyst having both convenience and increased activity. The amount of the catalyst preferably ranges from 0.01 to 2 molar equivalents, more preferably ranges from 0.03 to 1.0 molar equivalents, and in particular, preferably ranges from 0.05 to 0.8 molar equivalents with respect to one molar equivalent of the functional group.

A solvent may or may not be used. When the reaction system has an extremely increased viscosity or is in the form of a solid or a non-uniform slurry mixture in accordance with the catalyst type, the amount of the catalyst, or the blending amount of glycidol, a suitable solvent may be used and a polymerization reaction can be carried out therein.

The polymerization temperature may be suitably determined in accordance with polymerization activity of the catalyst used, concentration of the functional group thereof, and the like, and ranges from −78 to 220° C., and more preferably ranges from −30 to 150° C.

In the aforementioned moiety, a small amount of an ethyleneoxy group and/or a propyleneoxy group may be present. The aforementioned groups are unstable with respect to oxidation and are easily decomposed to give a carbonyl functional decomposed product. For this reason, the amount of the aforementioned groups is preferably not more than 0.5 molar equivalents with respect to one molar equivalent of a polyglycerol group, and more preferably not more than 0.2 molar equivalents. They can be easily produced by adding a specified amount of ethylene oxide and/or propylene oxide in the aforementioned polymerization reaction to perform copolymerization.

The aforementioned organohydrogenpolysiloxane is preferably represented by the following average unit formula (11):

$$R^2_a H_b SiO_{(4-a-b)/2} \quad (11)$$

wherein
$R^2$ represents a substituted or non-substituted monovalent hydrocarbon group containing no aliphatic unsaturated bond; and
$1.0 \leq a \leq 2.5$, and $0.001 \leq b \leq 1.5$.

Examples of $R^2$ are the same as described above, and the form thereof may be linear, branched, or cyclic. In addition, the number average molecular weight of the organohydrogenpolysiloxane preferably ranges from 300 to 700,000, more preferably ranges from 300 to 200,000, and more preferably ranges from 1,000 to 20,000.

As the addition reaction catalyst, a catalyst known by a person skilled in the art can be used. A platinum catalyst or a rhodium catalyst is preferably used. More particularly, chloroplatinic acid, an alcohol solution of chloroplatinic acid, a chloroplatinic acid-vinylsiloxane complex or the like is preferably used. The usage amount of the catalyst can be a catalytic amount. In particular, the amount of platinum or rhodium is not more than 50 ppm, and preferably not more than 20 ppm.

In the case of producing the partially hydrocarbon group-blocked (poly)glycerol-modified polysiloxane, the charging molar ratio of the aliphatic unsaturated bond with respect to the hydrogen atom binding to the silicon atom preferably ranges from 0.5 to 2.0, and more preferably ranges from 0.8 to 1.2. When it is desirable to completely react the hydrogen atoms binding to the silicon atoms, the aforementioned ratio preferably ranges from 1.0 to 2.0 and more preferably ranges from 1.0 to 1.5.

The reaction temperature is not particularly limited as long as the aforementioned addition reaction can proceed, and the reaction can be carried out at room temperature or under heating. In order to increase the reaction rate, the reaction is preferably carried out under heating. The reaction temperature preferably ranges from 50 to 200° C. In addition, the development of the reaction can be known by analyzing the reaction solution by means of a gas chromatography analysis, an infrared spectroscopic analysis, a nuclear magnetic resonance analysis or the like, and following the remaining index of the raw material, and the content index of the silicon atom-bonded hydrogen atom or the aliphatic unsaturation group in the reaction system.

The aforementioned addition reaction may be carried out in an organic solvent, if necessary. As examples of the organic solvent, mention may be made of, for example, an aliphatic alcohol such as methanol, ethanol, 2-propanol, butanol or the like; an aromatic hydrocarbon such as toluene, xylene, or the like; an aliphatic or alicyclic hydrocarbon such as n-pentane, n-hexane, cyclohexane or the like; a halogenated hydrocarbon such as dichloromethane, chloroform, carbon tetrachloride or the like; and the like. In order to completely react the silicon atom-bonded hydrogen atom, or alternatively, completely eliminate the silicon atom-bonded hydrogen atom, an after-treatment may be carried out by means of a method such as a method of reacting the remaining silicon atom-bonded hydrogen atom with a compound having a double bond such as 1-hexene or the like, or a method of dehydrogenating the silicon atom-bonded hydrogen atom by adding an alkali substance such as sodium hydroxide or the like.

After the reaction is completed, unreacted components, organic solvents and the like are removed. Thereby, the objective partially hydrocarbon group-blocked (poly)glycerol-modified polysiloxane can be obtained.

The aforementioned hydrosilylation reaction may be carried out in a batch type or a continuous type. In the case of carrying out the reaction in the continuous type, as described in Japanese Unexamined Patent Application, First Publication No. 2001-294666, a method in which the reaction can be carried out in a cylindrical reactor having a stirring means-and-continuous plug flow means therein is preferably used.

After the addition reaction is completed, in particular, in the case of using an organic solvent, materials having low boiling points after the aforementioned after-treatment is carried out are removed by heating under reduced pressure. Thereby, a novel partially hydrocarbon group-blocked (poly) glycerol-modified polysiloxane of the present invention can be obtained.

The partially hydrocarbon group-blocked (poly)glycerol-modified polysiloxanes of the present invention can be applied to various usages. In particular, they are preferable as raw materials for all cosmetics externally applied to skin or hair. In this case, the blending amount of the aforementioned polysiloxane preferably ranges from 0.1 to 40% by weight of the total weight of the cosmetic.

In the cosmetics of the present invention, components commonly used in cosmetics within a range which does not impair the effects of the present invention, such as water, powders, alcohols, water-soluble polymers, film-forming agents, resins, oil agents, oil-soluble gelling agents, organo-modified clay minerals, surfactants, UV absorbers, humectants, preservatives, antimicrobial agents, perfumes, salts, antioxidants, pH adjustors, chelating agents, fresheners, anti-inflammatory agents, skin-beautifying agents (such as whitening agents, cell activators, agents for ameliorating skin roughness, blood circulation promoters, astringents, antiseborrheic agents and the like), vitamins, amino acids, nucleic acids, hormones, clathrate compounds, and the like can be added. They are not particularly limited.

With respect to powders, there is no restriction on the form thereof (sphere, needle, plate, or the like), the particle size (aerosol, microparticle, pigment-grade, or the like), and the particle structure (porous, non-porous or the like) thereof, and any one thereof can be used, as long as the powders are commonly used in cosmetics. For example, as examples thereof, mention may be made of inorganic powders, organic powders, surfactant metal salt powders, colored pigments, pearl pigments, metal powder pigments, natural pigments and the like.

More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, silica, and the like.

As examples of organic powders, mention may be made of polyamide powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, Nylon® powder, Nylon® 12, Nylon® 6, silicone powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine and the like.

As examples of surfactant metal salt powders (metallic soaps), mention may be made of zinc stearate, aluminum stearate, calcium stearate, magnesium stearate, zinc myristate, magnesium myristate, zinc cetylphosphate, calcium cetylphosphate, sodium zinc cetylphosphate, and the like.

As examples of colored pigments, mention may be made of inorganic red pigments such as iron oxide, iron hydroxide, iron titanate and the like; inorganic blown pigments such as gamma-iron oxide and the like; inorganic yellow pigments such as yellow iron oxide, ocher, and the like; inorganic black pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; and synthetic resin powders such as laked tar pigments, laked natural pigments and complexed powders thereof, and the like.

As examples of pearl pigments, mention may be made of titanium oxide-coated mica, bismuth oxychloride, titanium oxide-coated bismuth oxychloride, titanium oxide-coated talc, fish scale foil, titanium oxide-coated colored mica, and the like.

As examples of metal powder pigments, mention may be made of aluminum powder, copper powder, stainless powder, and the like.

As examples of tar pigments, mention may be made of Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like.

As examples of natural pigments, mention may be made of carminic acid, laccaic acid, carthamin, brazilin, crocin, and the like. The aforementioned powders may be complexed or treated with a general oil agent, a silicone oil, a fluorine compound, a surfactant, or the like within a range which does not impair the effects of the present invention.

In addition, they can be used alone or in combination with two or more types thereof, if necessary.

As examples of alcohols, mention may be made of lower alcohols such as ethanol, isopropanol and the like; sugar alcohols such as sorbitol, maltose, and the like; and the like.

As examples of sterols, mention may be made of cholesterol, sitosterol, phytosterol, lanosterol and the like.

As examples of water-soluble polymers, mention may be made of vegetable-based polymers such as gum Arabic, tragacanth, galactan, carob gum, guar gum, Karaya gum, carrageenan, pectin, agar, quince seed, starch (rice, corn, potato, or wheat), algal colloide, tragacanth gum, locust bean gum, and the like, microorganism-based polymers such as xanthan gum, dextran, succinoglucan, pullulan, and the like; animal-based polymers such as collagen, casein, albumin, gelatin, and the like; starch-based polymers such as carboxymethyl starch, methylhydroxypropyl starch, and the like; cellulose-based polymers such as methylcellulose, ethylcellulose, methylhydroxypropylcellulose, carboxymethylcellulose, hydroxymethylcellulose, hydroxypropylcellulose, nitrocellulose, sodium cellulose sulfate, sodium carboxymethylcellulose, crystalline cellulose, cellulose powder, and the like; alginate-based polymers such as sodium alginate, propylene glycol alginate and the like; vinyl-based polymers such as polyvinyl methyl ether, carboxyvinyl polymer and the like; polyoxyethylene-based polymers; polyoxyethylene polyoxypropylene copolymer-based polymers; acrylic polymers such as sodium polyacrylate, polyethyl acrylate, polyacrylamide and the like; polyethylene imine; cationic polymers; and inorganic water-soluble polymers such as bentonite, aluminum magnesium silicate, montmorillonite, bidelite, nontronite, saponite, hectorite, silicic acid anhydride and the like.

As examples of film-forming agents, mention may be made of, for example, polyvinyl alcohol, polyvinylpyrrolidone and the like.

As oil agents, any oil agents in the form of a solid, semisolid or liquid can be used as long as they are commonly used in cosmetics. For example, as examples of natural animal or vegetable fats and oils and semi-synthetic fats and oils, mention may be made of avocado oil, linseed oil, almond oil, ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, squalene, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, lanolin fatty acid isopropyl ester, hexyl laurate, POE lanolin alcohol ether, POE lanolin alcohol acetate, lanolin fatty acid polyethylene glycol, POE hydrogenated lanolin alcohol ether, egg yolk oil, and the like.

As examples of hydrocarbon oils, mention may be made of ozocerite, squalane, squalene, ceresin, paraffin, paraffin wax, liquid paraffin, pristane, polyisobutylene, microcrystalline wax, vaseline, and the like.

As examples of higher fatty acids, mention may be made of lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As examples of higher alcohols, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerol ether (batyl alcohol), monooleyl glyceryl ether (selachyl alcohol) and the like.

As examples of ester oils, mention may be made of diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, diisostearyl malate, and the like.

As examples of glyceride oils, mention may be made of acetoglyceryl, glyceryl triisooctanoate, glyceryl triisostearate, glyceryl triisopalmitate, glyceryl monostearate, glyceryl di-2-heptylundecanoate, glyceryl trimyristate, diglyceryl myristate isostearate, and the like.

As examples of silicone oils, mention may be made of organopolysiloxanes having a low viscosity to a high viscosity such as dimethylpolysiloxane, methylphenylpolysiloxane, methylhydrogenpolysiloxane, copolymers of dimethylsiloxane and methylphenylsiloxane and the like; cyclosiloxanes such as octamethylcyclotetrasiloxane, decamethylcyclopentasiloxane, dodecamethylcyclohexasiloxane, tetramethyltetrahydrogencyclotetrasiloxane, tetramethyltetraphenylcyclotetrasiloxane, and the like; silicone rubbers such as dimethylpolysiloxane in the form of a rubber having a high degree of polymerization, copolymer of dimethylsiloxane and methylphenylsiloxane in the form of a rubber, and the like; and cyclosiloxane solutions of silicone rubbers, trimethylsiloxysilicic acid, cyclosiloxane solutions of trimethylsiloxysilicic acid, higher alkoxy-modified silicones such as stearoxysilicone and the like, higher fatty acid-modified silicones, alkyl-modified silicones, amino-modified silicones, fluorine-modified silicones, silicone resins; and the like.

As examples of fluorine-based oils, mention may be made of perfluoropolyether, perfluorodecaline, perfluorooctane and the like.

The aforementioned oil agents can be used alone or in combination with two or more types thereof.

As examples of oil-soluble gelling agents, mention may be made of metallic soaps such as aluminum stearate, magnesium stearate, zinc myristate and the like; amino acid derivatives such as N-lauroyl-L-glutamic acid, alpha, gamma-di-n-butylamine, and the like; dextrin fatty acid esters such as dextrin palmitate, dextrin stearate, dextrin 2-ethylhexanoate palmitate, and the like; sucrose fatty acid esters such as sucrose palmitate, sucrose stearate, and the like; benzylidene derivatives of sorbitol such as monobenzylidene sorbitol, dibenzylidene sorbitol, and the like; and the like.

As examples of organo-modified clay minerals, mention may be made of, for example, dimethylbenzyldodecylammonium montmorillonite clay, dimethyldioctadecylammonium montmorillonite clay, and the like. They can be used alone or in combination with two or more types thereof, if necessary.

As surfactants, there are anionic, cationic, nonionic and amphoteric surfactants, and in particular, they are not limited. Any surfactants can be used as long as they are commonly used in cosmetics. As examples of anionic surfactants, mention may be made of fatty acid soaps such as sodium stearate, palmitic acid triethanol amine and the like; alkyl ether carboxylic acids and salts thereof; carboxylates of condensates of amino acids and fatty acids and the like; alkylsulfonic acids; alkenesulfonates; sulfonates of fatty acid esters; sulfonates of fatty acid amides; sulfonates of alkylsulfonic acid salts and formalin condensates thereof; alkyl sulfuric acid esters; secondary higher alcohol sulfuric acid esters; alkyl and allyl ether sulfuric acid esters; sulfuric acid esters of fatty acid esters; sulfuric acid esters of fatty acid alkylolamides; sulfuric acid esters of Turkey red oil and the like; alkylphosphates; ether phosphates; alkyl allyl ether phosphates; amidophosphates; N-acylamino acid-based surfactants and the like.

As examples of cationic surfactants, mention may be made of alkylamine salts, amine salts of polyamines and aminoalcohol fatty acid derivatives, and the like, alkyl quaternary ammonium salts, aromatic quaternary ammonium salts, pyridinium salts, imidazolium salts and the like.

As examples of nonionic surfactants, mention may be made of sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene polyoxypropylene alkyl ether, polyoxyethylene alkylphenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene/alkyl-co-modified organopolysiloxane, alkanolamide, sugar ethers, sugar amides, and the like.

As examples of amphoteric surfactants, mention may be made of betaine, aminocarboxylic acid salts, imidazoline derivatives, and the like.

As examples of UV absorbers, mention may be made of benzoic acid-based UV absorbers such as para-aminobenzoic acid and the like; anthoranilic acid-based UV absorbers such as methyl anthoranilate and the like; salicylic acid-based UV absorbers such as methyl salicylate and the like; cinnamic acid-based UV absorbers such as octyl paramethoxycinnamate and the like; benzophenone-based UV absorbers such as 2,4-dihydroxybenzophenone and the like; urocanic acid-based UV absorbers such as ethyl urocanoate and the like; dibenzoylmethane-based UV absorbers such as 4-t-butyl-4'-methoxy-dibenzoylmethane and the like; and the like.

As examples of humectants, mention may be made of glycerol, sorbitol, propylene glycol, dipropylene glycol, 1,3-butylene glycol, glucose, xylitol, maltitol, polyethylene glycol, hyaluronic acid, chondroitin sulfate, pyrrolidone carboxylic acid salt, pyrrolidone carboxylic acid salt, polyoxyethylene methylglucoside, polyoxypropylene methylglucoside and the like.

As examples of preservatives and antimicrobial agents, mention may be made of alkyl paraoxybenzoates, benzoic acid, sodium benzoate, sorbic acid, potassium sorbate, phenoxyethanol, and the like.

As examples of antimicrobial agents, mention may be made of benzoic acid, salicylic acid, carbolic acid, sorbic acid, alkyl paraoxybenzoates, parachlorometacresol, hexachlorophene, benzalkonium chloride, chlorhexidine chloride, trichlorocarbanilide, photosensitizers, phenoxyethanol and the like.

As examples of antioxidants, mention may be made of tocopherol, butylhydroxyanisole, dibutylhydroxytoluene, phytic acid, and the like.

As examples of pH adjustors, mention may be made of lactic acid, citric acid, glycolic acid, succinic acid, tartaric acid, dl-malic acid, potassium carbonate, sodium hydrogencarbonate, ammonium hydrogencarbonate, and the like.

As examples of chelating agents, mention may be made of alanine, sodium edetate, sodium polyphosphate, sodium metaphosphate, phosphoric acid, and the like.

As examples of freshening agents, mention may be made of L-menthol, camphor and the like.

As examples of anti-inflammatory agents, mention may be made of allantoin, glycyrrhetinic acid, glycyrrhizinic acid, tranexamic acid, azulene, and the like.

As examples of skin-beautifying components, mention may be made of whitening agents such as placenta extracts, arbutin, glutathione, saxifrageous extracts and the like; cell activators such as royal jelly, photosensitizers, cholesterol derivatives, extracts from calf blood, and the like; agents for ameliorating skin roughness; blood circulation promoters such as nonylic acid vanillylamide, benzyl nicotinate, betabutoxyethyl nicotinate, capsaicin, gingerone, cantharides tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; and the like.

As examples of vitamins, mention may be made of vitamin As such as vitamin A oil, retinol, retinol acetate, retinol palmitate and the like; vitamin Bs such as vitamin B2s such as riboflavin, riboflavin lactate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl-2-sulfate, dipotassium L-ascorbyl phosphate and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate, nicotinic acid amide and the like; pantothenic acids such as calcium pantothenate, D-pantothenyl alcohol, pantothenyl ethyl ether, acetyl pantothenyl ethyl ether and the like; biotin; and the like.

As examples of amino acids, mention may be made of glycine, valine, leucine, isoleucine, serine, threonine, phenylalanine, arginine, lysine, aspartic acid, glutamic acid, cystine, cysteine, methionine, tryptophan, and the like.

As examples of nucleic acids, mention may be made of deoxyribonucleic acid and the like.

As examples of hormones, mention may be made of estradiol, ethenylestradiol and the like.

In the present invention, as examples of cosmetics, mention may be made of skin care compositions such as a cosmetic lotion, a milky lotion, a cream, a composition for use in cleansing, a composition for use in massaging, a cleanser, an antiperspirant, a deodorant and the like; makeup compositions such as a foundation, a base for making up, a blusher, an eye shadow, a mascara, an eyeliner, a lipstick and the like; compositions for use on hair such as a shampoo, a rinse, a treatment and the like; and the like. The form thereof may be selected from various forms such as liquid, emulsion, solid, paste, gel, spray and the like.

EXAMPLES

Reference Example

As a result of $^{13}$C nuclear magnetic resonance ($^{13}$C NMR) analysis of a commercially available glycidyl methyl ether, it could be seen that 3.4% by mole (13,700 ppm) of chloride corresponding to epichlorhydrin was contained. Sodium hydroxide pulverized by means of a hammer (having an average particle size of not less than 300 μm), in an amount of 25 g, was placed in 500 g of the aforementioned glycidyl methyl ether. The mixture was heated and stirred for 3 hours at 80° C. under a nitrogen atmosphere. Subsequently, simple distillation was carried out with a degree of reduced pressure ranging from 40 to 50 mmHg, and 360 g of a fraction was obtained. As a result of NMR analysis thereof, purity was 99.9%, and no signals due to impurities were observed. 5% by weight of molecular sieves 4A was added to the purified glycidyl methyl ether to dehydrate. The dehydrated product was used as a raw material for polymerization.

Example 1

Ethylene glycol monoallyl ether, in an amount of 1.88 g (18.4 mmol), and potassium t-butoxide, in an amount of 0.10 g (0.88 mmol), were mixed and the mixture was heated at 105° C. under a nitrogen atmosphere. A mixture of 10.9 g (147.2 mmol) of glycidol and 6.5 g (73.6 mmol) of glycidyl methyl ether purified in the aforementioned Reference Example was slowly added dropwise thereto over 3.5 hours (molar ratio of ethylene glycol monoallyl ether:glycidol:glycidyl methyl ether=1:8:4). After completion of the dropwise addition, the mixture was heated and stirred for 3 hours at 120° C. The mixture was cooled to room temperature, and 0.06 g of acetic acid was added thereto to stop the polymerization. Toluene in an amount of 10 g was added thereto, and KYOWADO 500 SN, which is a hydrotalcite-based absorbent manufactured by Kyowa Chemical Industry Co., Ltd., was added thereto, and the mixture was stirred for 2 hours. After the mixture was filtered, the materials with low boiling points were removed from the filtrate by heating under reduced pressure. Thereby, 18.8 g (yield=98%) of a transparent liquid polymer was obtained. The polymer was slightly heated, and thereby, it could be easily taken out from the reactor. The number average molecular weight thereof on the basis of standard polystyrene, measured by means of gel permeation chromatography (GPC) by a refractive index detector with chloroform as a solvent was 249 and the degree of dispersion was 1.785. In addition, from the results of $^{13}$C-nuclear magnetic resonance ($^{13}$C-NMR) analysis shown in FIG. 1, the present polymer was a one-terminal allyloxyethoxy group-blocked partially-methylated polyglycerol, and the molar ratio of carbinol group:methoxy group was 69:21. In addition, the signal of a —CH$_2$—CH(—CH$_2$O—)O— group showing a branched structure was observed at 78 to 81 ppm.

Examples 2 to 7

In the same manner as described in Example 1, a polymerization reaction was carried out with the composition shown in a table described below, and the corresponding one-terminal-allyloxyethoxy group-blocked partially-methylated polyglycerol was obtained. The results are shown in Table 1 and Table 2.

TABLE 1

| | Example 2 | Example 3 | Example 4 | Example 5 |
|---|---|---|---|---|
| Ethylene glycol monoallyl ether (A) (g) | 1.88 | 1.88 | 1.88 | 1.88 |
| Potassium t-butoxide (g) | 0.1 | 0.1 | 0.1 | 0.1 |
| Glycidyl methyl ether (B) (g) | 3.24 | 9.72 | 12.96 | 16.21 |
| Glycidol (C) (g) | 13.63 | 8.17 | 5.45 | 2.73 |
| Number average molecular weight | —* | 470 | 1123 | 1328 |
| Degree of dispersion | —* | 1.721 | 1.378 | 1.388 |

TABLE 1-continued

|  | Example 2 | Example 3 | Example 4 | Example 5 |
|---|---|---|---|---|
| Molar ratio (A:B:C) | 1:2:10 | 1:6:6 | 1:8:4 | 1:10:2 |
| Molar ratio (OH group:CH$_3$ group) | 85:15 | 54:46 | 38:62 | 23:77 |

*insoluble in chloroform

TABLE 2

|  | Example 6 | Example 7 |
|---|---|---|
| Ethylene glycol monoallyl ether (A) (g) | 3.76 | 0.94 |
| Potassium t-butoxide (g) | 0.1 | 0.1 |
| Glycidyl methyl ether (B) (g) | 12.96 | 12.96 |
| Glycidol (C) (g) | 5.45 | 5.45 |
| Number average molecular weight | 753 | 1430 |
| Degree of dispersion | 1.397 | 1.445 |
| Molar ratio (A:B:C) | 1:4:2 | 1:16:8 |
| Molar ratio (OH group:CH$_3$ group) | 43:57 | 36:64 |

Example 8

Ethylene glycol monoallyl ether, in an amount of 1.88 g (18.4 mmol), and potassium t-butoxide, in an amount of 0.10 g (0.88 mmol), were mixed, and the mixture was heated at 120° C. under a nitrogen atmosphere. Glycidol, in an amount of 5.45 g (73.6 mmol), was slowly added dropwise thereto over 1.5 hours at 115 to 120° C. After completion of the dropwise addition, the mixture was heated and stirred for 2 hours at 120° C. to complete polymerization. Subsequently, 12.96 g (147.2 mmol) of glycidyl methyl ether purified in the aforementioned Reference Example was added thereto. Subsequently, the mixture was heated and stirred for 3 hours at 120 to 130° C. to complete block copolymerization (molar ratio of ethylene glycol monoallyl ether:glycidol:glycidyl methyl ether=1:4:8). The mixture was cooled to room temperature, and 0.06 g of acetic acid was added thereto, to stop the polymerization. Toluene in an amount of 10 g was added thereto, and KYOWADO 500 SN, which is a hydrotalcite-based absorbent manufactured by Kyowa Chemical Industry Co., Ltd., was added thereto, and the mixture was stirred for 2 hours. After the mixture was filtered, the materials with low boiling points were removed from the filtrate by heating under reduced pressure. Thereby, 19.9 g (yield=98%) of a transparent liquid polymer was obtained. The number average molecular weight thereof on the basis of standard polystyrene, measured by means of gel permeation chromatography (GPC) by a refractive index detector with chloroform as the solvent was 1,412 and the degree of dispersion was 1.271. In addition, from the results of $^{13}$C-nuclear magnetic resonance ($^{13}$C-NMR) analysis, the present polymer was a one-terminal allyloxyethoxy group-blocked partially-methylated polyglycerol, and the molar ratio of carbinol group:methoxy group was 38:62. In addition, the signal of a —CH$_2$—CH(—CH$_2$O—)O— group showing a branched structure was observed at 78 to 81 ppm.

The reaction scheme in Example 8 is generally described as follows:

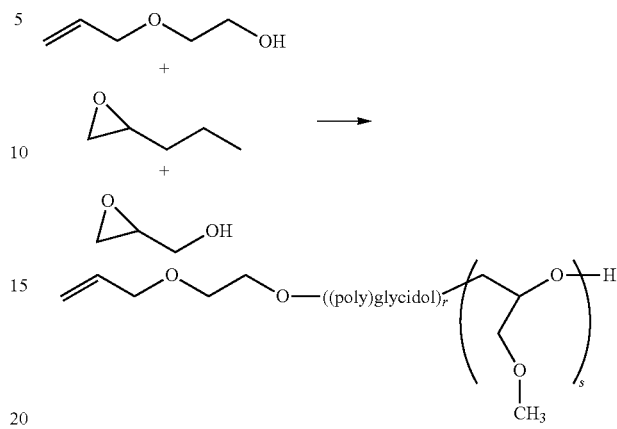

Example 9 and Example 10

The corresponding one-terminal allyloxyethoxy group-blocked partially-ethylated polyglycerols were obtained by carrying out a polymerization reaction in the same manner as described in Examples 1 to 7 with the compositions described below using glycidyl ethyl ether instead of glycidyl methyl ether. The results are shown in Table 3.

TABLE 3

|  | Example 9 | Example 10 |
|---|---|---|
| Ethylene glycol monoallyl ether (A) (g) | 1.88 | 1.17 |
| Potassium t-butoxide (g) | 0.1 | 0.1 |
| Glycidyl methyl ether (B) (g) | 7.52 | 7.00 |
| Glycidol (C) (g) | 10.90 | 5.07 |
| Number average molecular weight | 339 | — |
| Degree of dispersion | 1.875 | — |
| Molar ratio (A:B:C) | 1:4:8 | 1:6:6 |
| Molar ratio (OH group:CH$_3$ group) | 38:62 | 54:46 |

Example 11

In a four-necked flask equipped with a stirrer, 7.5 g (7.16 mmol) of the one-terminal allyloxyethoxy group-blocked partially-methylated polyglycerol synthesized in Example 1, 1.71 g (1.99 mmol, SiH=5.97 mmol) of a copolymer of a polydimethylsiloxane and a polymethylhydrogensiloxane, represented by the following formula (I):

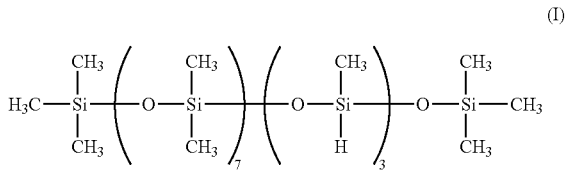

Figure 2:
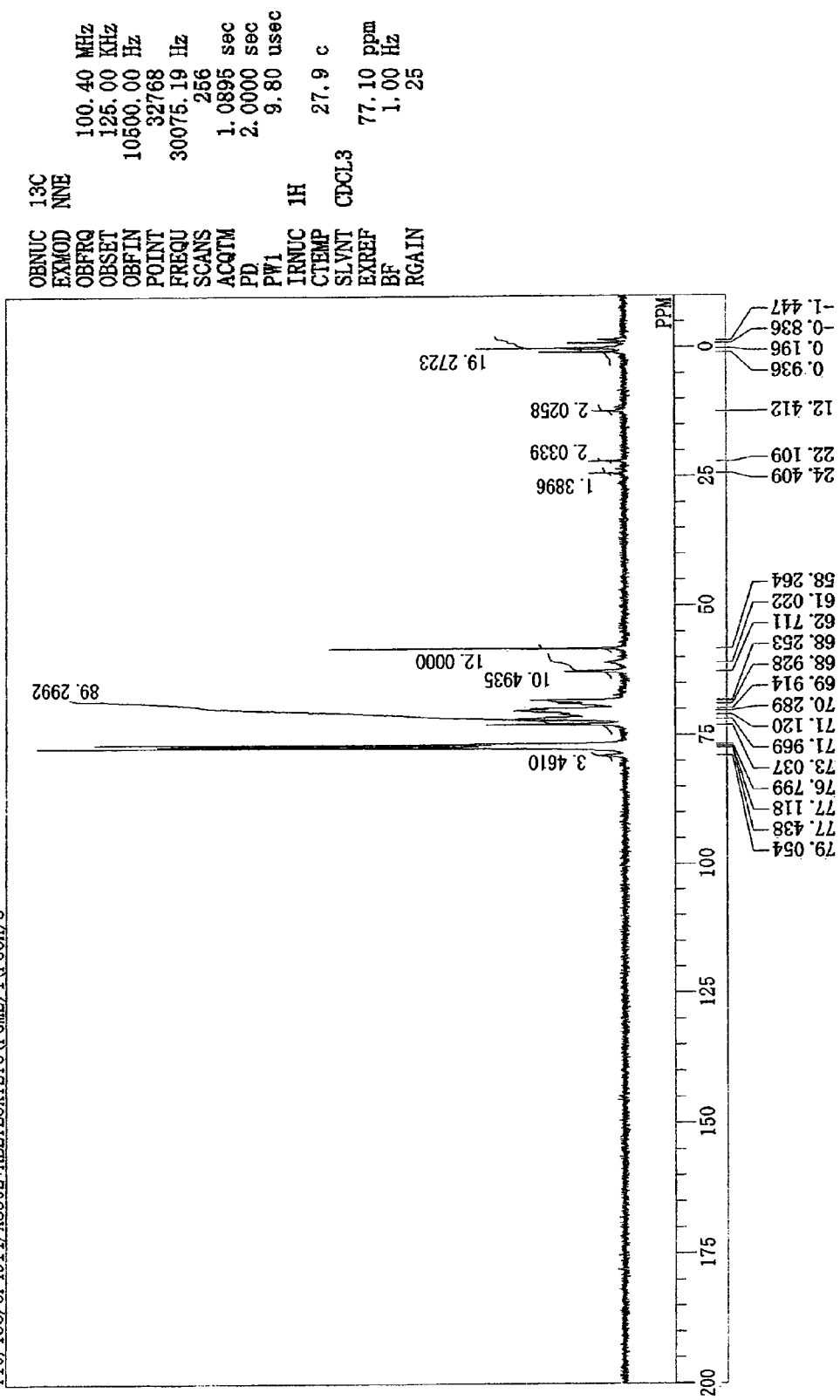
FIG. 2 is a $^{13}$C NMR chart of a partially methylated polyglycerol graft-type polysiloxane produced in Example 11.
Figure 3:
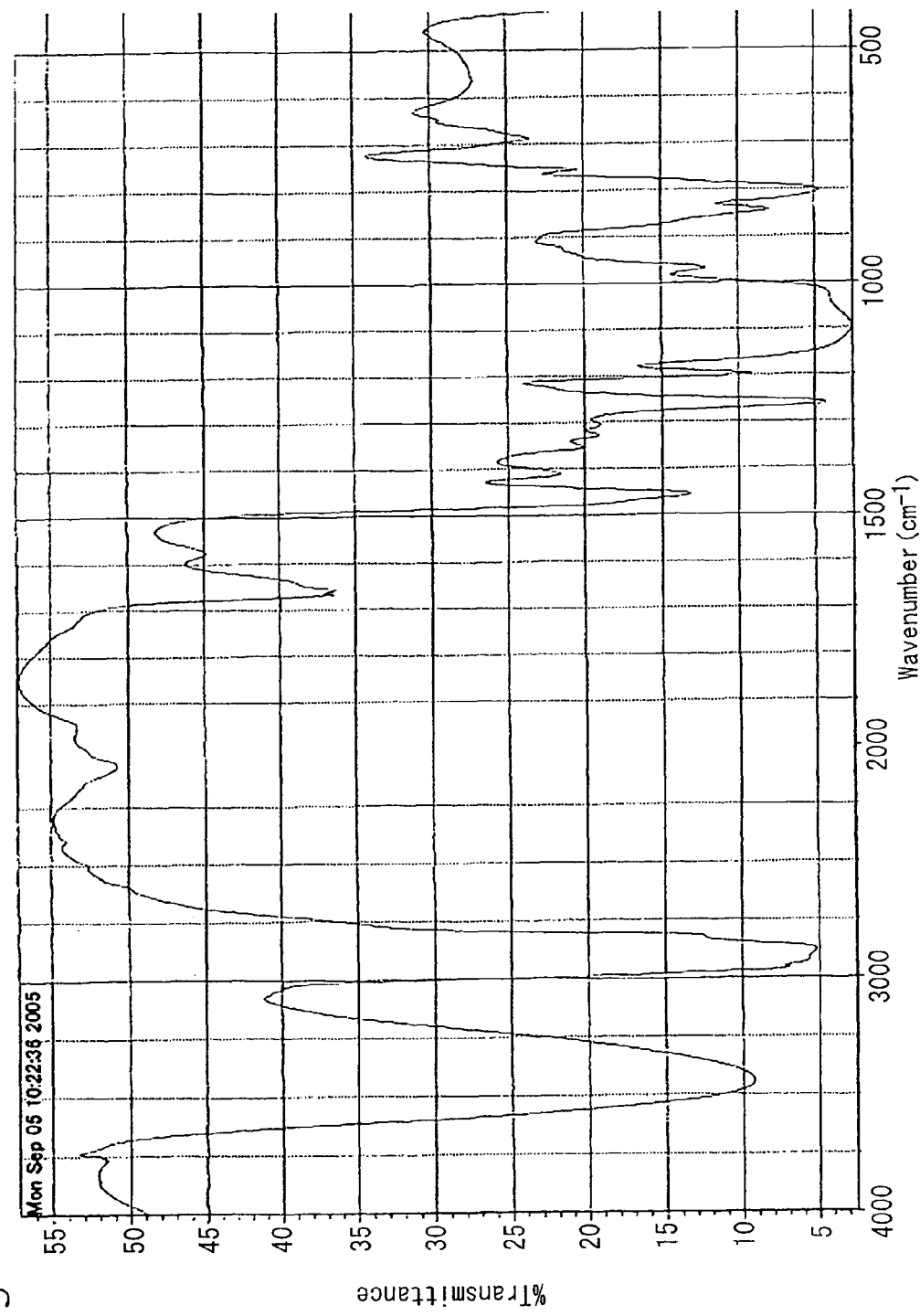
FIG. 3 is an IR chart of a partially methylated polyglycerol graft-type polydimethylsiloxane produced in Example 16 which was subjected to heat deterioration at 50° C. for 3 weeks in air (see Example 21).
Figure 4:
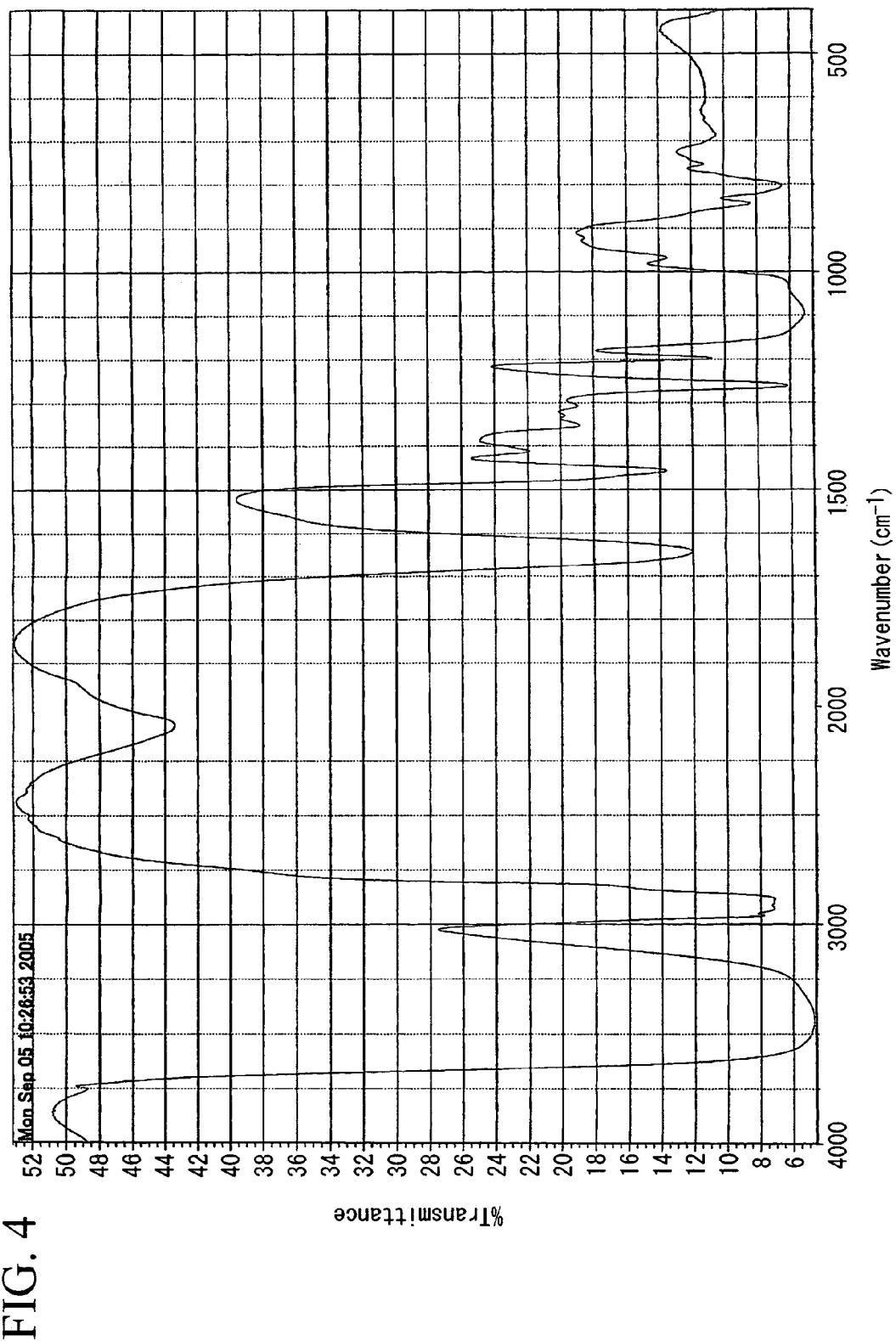
FIG. 4 is an IR chart of a mixture of a partially methylated polyglycerol graft-type polydimethylsiloxane produced in Example 16 with a buffer solution at pH 6 which was subjected to heat deterioration at 50° C. for 3 weeks in air (see Example 21).
Figure 5:
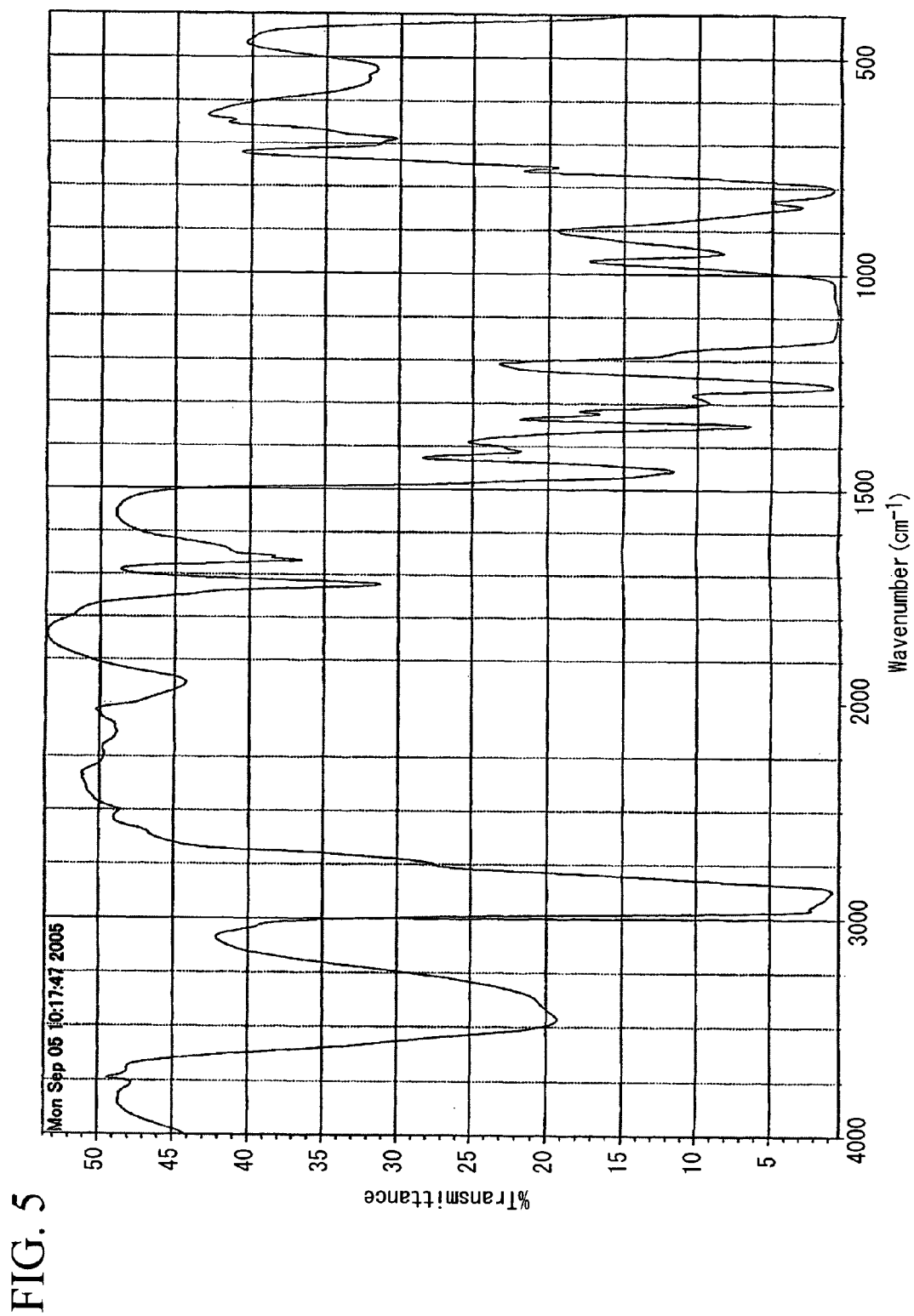
FIG. 5 is an IR chart of a polyoxyethylene graft-type polydimethylsiloxane produced in Comparative Example 1 which was subjected to heat deterioration at 50° C. for 3 weeks in air.
Figure 6:
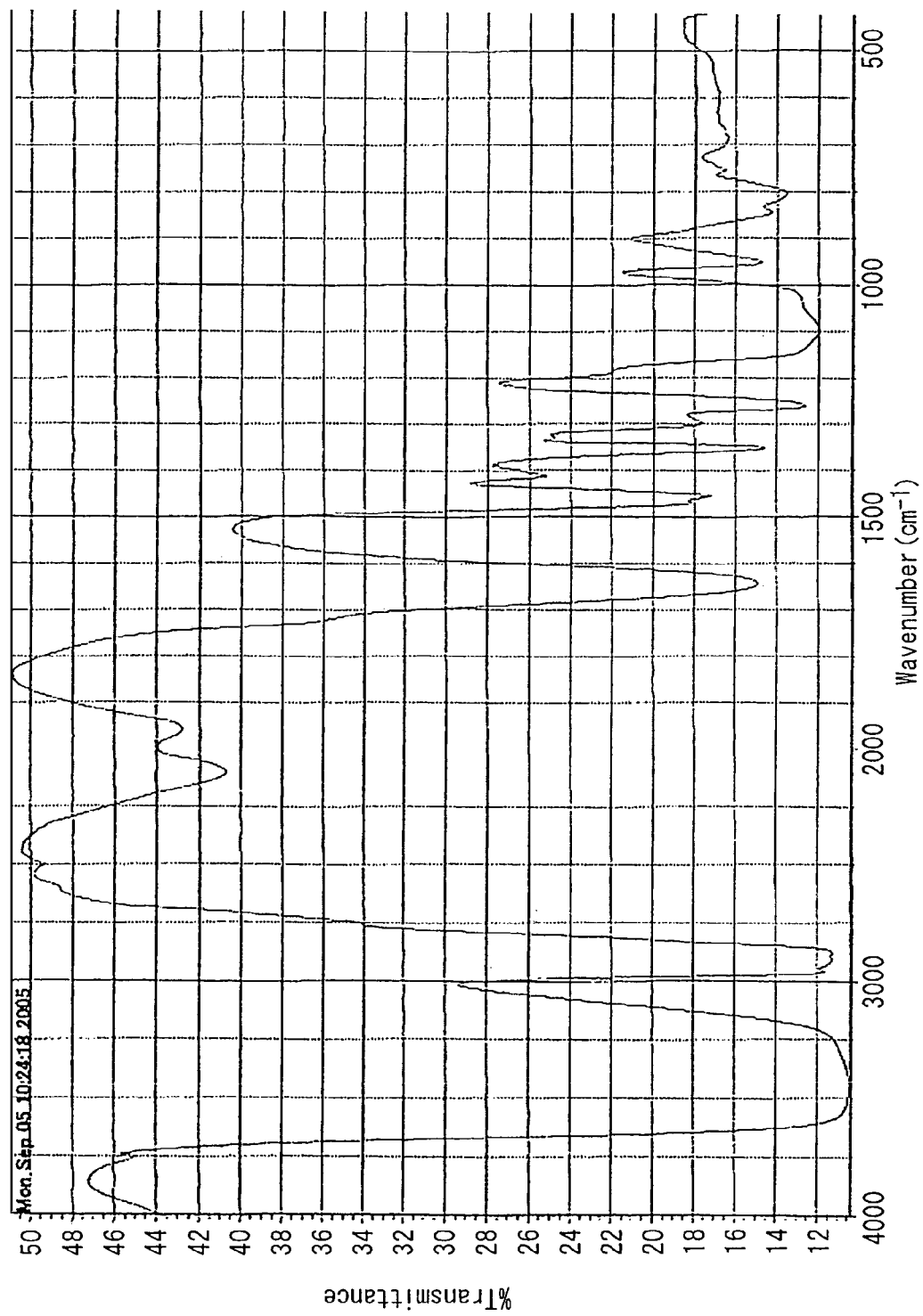
FIG. 6 is an IR chart of a mixture (concentration=80% by weight) of a polyoxyethylene graft-type polydimethylsiloxane produced in Comparative Example 1 with a buffer solution at pH 6 which was subjected to heat deterioration at 50° C. for 3 weeks in air.

(I)

and 9.2 g of isopropyl alcohol were mixed. In addition, a complex of platinum and 1,3-divinyl-tetramethyldisiloxane was mixed therewith so that the amount of the platinum metal was 5 ppm. The mixture was stirred for 3 hours at 80° C. As a result of infrared (IR) absorption analysis thereof by sampling, the characteristic absorption of the silicon atom-bonding hydrogen atom disappeared, and the reaction was completed. The materials with low boiling points were removed by heating and distilling under reduced pressure. Thereby, 8.6 g (yield=93%) of a pale yellow transparent polymer was obtained. As a result of $^{29}Si$ and $^{13}C$ nuclear magnetic resonance (NMR) analysis of the polymer (see FIG. 2), it can be seen that the polymer was a partially-methylated polyglycerol graft-type polydimethylsiloxane. The number average molecular weight thereof on the basis of standard polystyrene, measured by means of gel permeation chromatography (GPC) by a refractive index detector with chloroform as the solvent was 188 and the degree of dispersion was 3.012. The obtained polysiloxane exhibited fluidity even at room temperature, and by slightly heating, the polysiloxane could be easily taken out from the reactor. In addition, the polysiloxane exhibited complete compatibility with water, and a transparent aqueous solution thereof could be obtained. As a result of measuring the cloud point after a 0.5% by weight aqueous solution was prepared and heated, the cloud point was not less than 80° C.

Examples 12 to 20

The corresponding partially-methylated or partially-ethylated polyglycerol graft-type polysiloxanes were obtained by carrying out a hydrosilylation reaction with the compositions described below using the one-terminal allyloxyethoxy group-blocked partially-alkylated polyglycerols synthesized in Examples 2 to 20. All of these polysiloxanes could be dissolved in water and provided transparent aqueous solutions. As the degree of methylation or the degree of ethylation is increased, the viscosity is reduced. In the case of having low viscosity, the polysiloxane could be taken out from the reactor even at room temperature. In addition, as the degree of methylation or the degree of ethylation increased, and the index of containing a carbinol group decreased, the cloud point decreased. The results are shown in Table 4 and Table 5.

TABLE 4

| | Example 12 | Example 13 | Example 14 | Example 15 | Example 16 |
|---|---|---|---|---|---|
| Copolymer of polydimethylsiloxane and polymethylhydrogensiloxane of formula (I) (g) | 1.76 | 1.67 | 1.62 | 1.58 | 2.97 |
| One-terminal allyloxyethoxy group-blocked partially-alkylated polyglycerol (g) | Example 2 7.5 | Example 3 7.5 | Example 4 7.5 | Example 5 7.5 | Example 6 7.5 |
| Platinum catalyst (ppm) | 5 | 5 | 5 | 5 | 5 |
| Toluene (g) | — | — | 4 | 4 | 4 |
| Isopropyl alcohol (g) | 9.3 | 9.2 | — | — | — |
| Number average molecular weight | —* | 521 | 1,836 | 2,142 | 1,303 |
| Degree of dispersion | —* | 2.47 | 1.914 | 2.434 | 2.445 |
| Cloud point (0.5% aqueous solution) | Not less than 80° C. | Not less than 80° C. | 79° C. | 58° C. | 25° C. |

*insoluble in chloroform

TABLE 5

| | Example 17 | Example 18 | Example 19 | Example 20 |
|---|---|---|---|---|
| Copolymer of polydimethylsiloxane and polymethylhydrogensiloxane of formula (I) (g) | 1.14 | 1.62 | 1.62 | 1.55 |
| One-terminal allyloxyethoxy group-blocked partially-alkylated polyglycerol (g) | Example 7 10 | Example 8 7.5 | Example 9 7.5 | Example 10 7.5 |
| Platinum catalyst (ppm) | 5 | 5 | 5 | 5 |
| Toluene (g) | 4 | 4 | 4 | 4 |
| Isopropyl alcohol (g) | — | — | — | — |
| Number average molecular weight | 1,963 | 2,383 | — | — |
| Degree of dispersion | 1.866 | 1.883 | — | — |
| Cloud point (0.5% aqueous solution) | Not less than 85° C. | Not less than 85° C. | 95° C. | 43° C. |

Example 21 and Comparative Example 1

The partially-methylated polyglycerol graft-type polydimethylsiloxane produced in Example 16 (Example 21), in an amount of 2 g, or a polyoxyethylene graft-type polydimethylsiloxane having a polysiloxane content index and a value of the measured molecular weight which were close to those of the polydimethylsiloxane produced in Example 16 (Comparative Example 1) having a structure shown by the following formula (II):

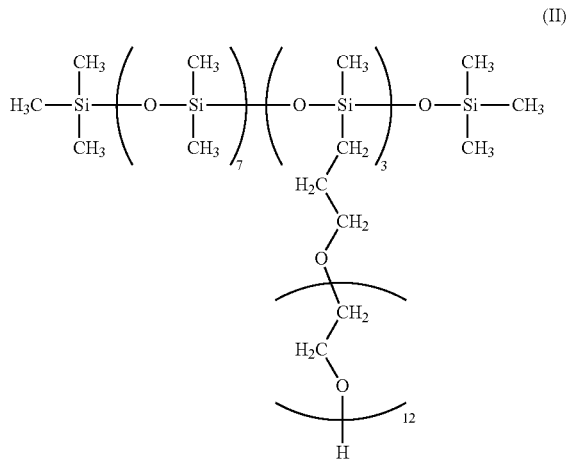

(II)

in an amount of 2 g, as a single material, as well as, a solution obtained by mixing each of the aforementioned Example 21 and Comparative Example 1 with a buffer solution at pH 6 so that the concentration of the aforementioned Example 21 or Comparative Example 1 was 80% by weight, in an amount of 2 g, were independently placed in a glass bottle with a volume of 30 cc and sealed under an air atmosphere, followed by subjecting them to a deterioration treatment by heating for 3 weeks in an oven at 50° C.

After the bottle was returned to room temperature, the presence of formaldehyde was checked by using a Formaldehyde Test Strip (TR) manufactured by Kanto Chemical Co., Inc., which is a test paper for selectively detecting formaldehyde. As a result, in both cases of the single material of Comparative Example 1 (polyoxyethylene graft-type polydimethylsiloxane) and the mixture thereof with the buffer solution at pH 6, yellowing was observed, and formaldehyde was detected. On the other hand, in both cases of the single material of Example 21 (partially-methylated polyglycerol graft-type polydimethylsiloxane produced in Example 16) and the mixture thereof with the buffer solution at pH 6, yellowing was not observed, and it could not be confirmed that formaldehyde was produced.

In addition, as a result of IR analysis after the deterioration test at 50° C., in both cases of the single material of Comparative Example 1 and the mixture thereof with the buffer solution at pH 6, characteristic absorption at 1,720 cm$^{-1}$ was observed. In addition, as the pH decreased, the absorption strength increased. From the aforementioned observation, it can be seen that, in particular, under an acidic condition, the polyoxyethylene graft-type polydimethylsiloxane was oxidation-decomposed, and a carbonyl-functional compound was easily produced. On the other hand, in both the case of the single material of Example 21 and the case of the mixture thereof with the buffer solution at pH 6, the characteristic absorption at 1,720 cm$^{-1}$ was hardly observed, and it can be seen that a carbonyl-functional compound was hardly produced (see FIG. 3 to FIG. 6).

Example 22

A partially-methylated polyglycerol graft-type polysiloxane was obtained by means of an addition reaction of the allyloxyethoxy group-blocked partially-methylated polyglycerol produced in Example 6 with a copolymer of a polydimethylsiloxane and a polymethylhydrogensiloxane represented by the following formula (III):

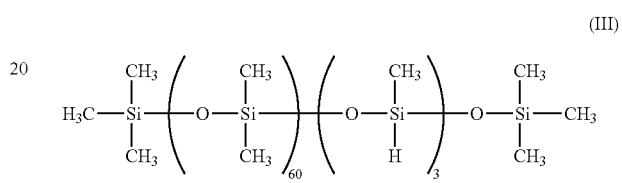

(III)

in the same manner as described in Example 11.

Example 23

A partially-methylated polyglycerol-polyoxypropylene (3) oleyl ether co-graft type polydimethylsiloxane (molar ratio of partially-methylated polyglycerol group:polyoxypropylene (3) oleyl ether group=5:8) was obtained by co-addition-reacting the allyloxyethoxy group-blocked partially methylated polyglycerol produced in Example 6 and a polyoxypropylene (3) allyl oleyl ether (RG-1252, manufactured by Nippon Nyukazai Co., Ltd.) with a copolymer of a polydimethylsiloxane and a polymethylhydrogensiloxane represented by the following formula (IV):

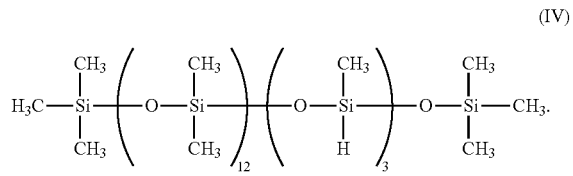

(IV)

Comparative Example 2

Glycidol was subjected to a ring-opening polymerization in the presence of glycerol monoallyl alcohol (molar ratio of glycerol monoallyl alcohol:glycidol=1:12) without using glycidyl methyl ether or glycidyl ethyl ether, and thereby, a one-terminal allyloxyethoxy group-blocked polyglycerol. The polyglycerol exhibited fluidity when heated, but did not exhibit fluidity at room temperature. The polyglycerol had a higher viscosity, as compared with those of the one-terminal allyloxyethoxy group-blocked partially-methylated polyglycerol and one-terminal allyloxyethoxy group-blocked partially-ethylated polyglycerol synthesized in the aforementioned Examples. Therefore, it was extremely difficult to be taken out from a reactor.

Subsequently, the polyglycerol was subjected to an addition reaction with the copolymer of polydimethylsiloxane and polymethylhydrogensiloxane of the aforementioned formula (I), and thereby, a partially-methylated polyglycerol graft-type polysiloxane was obtained. The polysiloxane also exhibited fluidity when heated, but did not exhibit much fluidity at room temperature. The polyglycerol had increased viscosity, as compared with the partially methylated polyglycerol graft-type polysiloxane and the partially-ethylated polyglycerol graft-type polysiloxane synthesized in the aforementioned Examples. Therefore, it was extremely difficult to take out the glycerol from the reactor.

Example 24

An eyeliner comprising the components described below was prepared.

TABLE 6

| | | % by weight |
|---|---|---|
| 1 | Octamethylcyclotetrasiloxane | Residual quantity |
| 2 | Partially-methylated polyglycerol graft-type polysiloxane of Example 22 | 3 |
| 3 | Silicone resin | 15 |
| 4 | Dioctadecyldimethylammonium salt-modified montmorillonite | 3 |
| 5 | Silicone-treated black iron oxide | 10 |
| 6 | 1,3-butylene glycol | 5 |
| 7 | Preservatives | q.s. |
| 8 | Perfume | q.s. |
| 9 | Purified water | 10 |

Silicone resin: 50% D5 solution of a silicone network compound having an [Me$_3$SiO$_{1/2}$]/[SiO$_2$] ratio of 0.8

Silicone-treated black iron oxide: heat-treated product after adding a methylhydrogenpolysiloxane in an amount of 2% with respect to black iron oxide Preparation Method A: Components 1 to 4 were mixed and Component 5 was added thereto, followed by uniformly mixing and dispersing therein.
B: Components 6 to 8 and 10 were mixed.
C: The aforementioned B was gradually added to the aforementioned A to emulsify them, followed by adding Component 9. Thereby, an eyeliner was obtained.

It can be seen that the eyeliner obtained as described above exhibited light spreading properties, provided easiness for drawing lines, imparted a pleasant cooling sensation and a refreshing sensation, imparted a sensation in use without stickiness, exhibited superior usability and superior stability without changing over time or without changing due to temperature, exhibited both superior water resistance and superior perspiration resistance, and exhibited good cosmetic durability.

Example 25

An eye shadow comprising the components described below was prepared.

TABLE 7

| | | % by weight |
|---|---|---|
| 1 | Decamethylpentasiloxane | 15 |
| 2 | Dimethylpolysiloxane (6 cS) | 10 |
| 3 | Partially-methylated polyglycerol graft-type polysiloxane of Example 22 | 2 |
| 4 | PEG (10) lauryl ether | 0.5 |
| 5 | Silicone-treated chromium oxide* | 6.2 |
| 6 | Silicone-treated ultramarine blue* | 4 |
| 7 | Silicone-treated titanium-coated mica* | 6 |
| 8 | Sodium chloride | 2 |
| 9 | Propylene glycol | 8 |
| 10 | Preservatives | q.s. |
| 11 | Perfume | q.s. |
| 12 | Purified water | Residual quantity |

*"Silicone-treated" = heat-treated after a methylhydrogenpolysiloxane was added in an amount of 3% with respect to the powder.

Preparation Method

A: Components 1 to 4 were mixed and Components 5 to 7 were added thereto, followed by uniformly dispersing therein.
B: Components 8 to 10 and 12 were uniformly dissolved.
C: The aforementioned B was gradually added to the aforementioned A under stirring to emulsify them, followed by adding Component 11 thereto. Thereby, an eye shadow was obtained.

It can be seen that the eye shadow obtained as described above exhibited light spreading properties, imparted no oily sensation or no powdery sensation, provided moisturizing properties, and imparted a refreshing sensation on use, as well as, at the same time, exhibited good water resistance, good water repellence and good perspiration resistance, exhibited cosmetic durability, and also had superior stability without changing over time or without changing due to temperatures.

Example 26

A suntan emulsion comprising the following components was prepared.

TABLE 8

| | | % by weight |
|---|---|---|
| 1 | Emulsifier composition* | 6 |
| 2 | Dimethylpolysiloxane (20 cS) | 49 |
| 3 | 1,3-butylene glycol | 5 |
| 4 | Sodium dehydroacetate | q.s. |
| 5 | Antioxidant | q.s. |
| 6 | Preservatives | q.s. |
| 7 | Perfume | q.s. |
| 8 | Purified water | Residual quantity |

*Emulsifier composition:
a. Partially-methylated polyglycerol graft-type polysiloxane of Example 22: 10 parts by weight
b. Dioctadecyldimethylammonium salt-modified montmorillonite: 10 parts by weight
c. Ethanol: 40 parts by weight Preparation Method A: Component a was dissolved in Component c, and Component b was added thereto B: The aforementioned A was stirred for one hour by means of a disper, followed by removing ethanol by means of an evaporator.

C: The aforementioned B was dried one whole day and night. Thereby, an emulsifier composition of Component 1 was obtained.

D: Component 1 obtained in the aforementioned C and Component 2 were mixed.

E: Components 3 to 6 and 8 were uniformly mixed.

F: The aforementioned E was gradually added to the aforementioned D under stirring to emulsify them, followed by adding Component 7 thereto. Thereby, a suntan emulsion was obtained.

It can be seen that the suntan emulsion obtained as described above exhibited fine texture, exhibited light spreading properties, imparted no stickiness or no oily sensation, provided moisturizing properties, and imparted a refreshing sensation on use, as well as, at the same time, exhibited good water resistance and good cosmetic durability, and had superior stability without changing over time or without changing due to temperature.

Example 27

A foundation comprising the following components was prepared.

TABLE 9

| | | % by weight |
|---|---|---|
| 1 | Decamethylcyclopentasiloxane | 45 |
| 2 | Dimethylpolysiloxane (6 cS) | 5 |
| 3 | Partially-methylated polyglycerol graft-type polysiloxane of Example 22 | 1.5 |
| 4 | Partially-methylated polyglycerol graft-type polysiloxane of Example 23 | 0.5 |
| 5 | Octadecyldimethylbenzylammonium salt-modified montmorillonite | 4 |
| 6 | Titanium oxide after hydrophobic treatment * | 10 |
| 7 | Talc oxide after hydrophobic treatment * | 6 |
| 8 | Mica oxide after hydrophobic treatment * | 6 |
| 9 | Red iron oxide after hydrophobic treatment * | 1.6 |
| 10 | Yellow iron oxide after hydrophobic treatment * | 0.7 |
| 11 | Black iron oxide after hydrophobic treatment * | 0.2 |
| 12 | Dipropylene glycol | 5 |
| 13 | Methyl paraoxybenzoate | 0.3 |
| 14 | 2-amino-2-methyl-1,3-propanediol | 0.2 |
| 15 | Hydrochloric acid | 0.1 |
| 16 | Perfume | q.s. |
| 17 | Water | Residual quantity |

* "after hydrophobic treatment" = heat treated after a methylhydrogenpolysiloxane in an amount of 2% with respect to the powder was added Preparation Method A: Components 1 to 5 were heated and mixed, and Components 6 to 11 were added thereto to form a uniform mixture.

B: Components 12 to 15 and 17 were heated and dissolved (pH of the aqueous system=9.0).

C: The aforementioned B was gradually added to the aforementioned A under stirring to emulsify them, and the emulsion was cooled, followed by adding Component 16 thereto. Thereby, a foundation was obtained.

It can be seen that the foundation obtained as described above exhibited fine texture, exhibited light spreading properties, imparted no stickiness or no oily sensation, provided moisturizing properties, and imparted a refreshing sensation on use, as well as, at the same time, exhibited good cosmetic durability, and had superior stability without changing over time or without changing due to temperature.

Example 28

A hair cream comprising the components described below was prepared.

TABLE 10

| | | % by weight |
|---|---|---|
| 1 | Decamethylcyclopentasiloxane | 10 |
| 2 | Methylphenylpolysiloxane | 5 |
| 3 | Squalane | 4 |
| 4 | Silicone resin * | 1 |
| 5 | Glyceryl dioleate | 2 |
| 6 | Partially-methylated polyglycerol graft-type polysiloxane of Example 22 | 4 |
| 7 | Sodium sorbitol sulfate | 1 |
| 8 | Sodium chondroitin sulfate | 1 |
| 9 | Sodium hyaluronate | 0.5 |
| 10 | Propylene glycol | 3 |
| 11 | Preservatives | 1.5 |
| 12 | Vitamin E acetate | 0.1 |
| 13 | Antioxidant | q.s. |
| 14 | Perfume | q.s. |
| 15 | Purified water | Residual quantity |

* Silicone resin: 50% D5 solution of a silicons network compound having an [Me$_3$SiO$_{1/2}$]/[SiO$_2$] ratio of 0.8.

Preparation Method

A: Components 1 to 6, 11 and 12 were heated and mixed.

B: Components 7 to 10 and 15 were heated and dissolved.

C: The aforementioned B was gradually added to the aforementioned A to emulsify them, and the emulsion was cooled, followed by adding Component 14 thereto. Thereby, a hair cream was obtained.

It can be seen that the hair cream obtained as described above exhibited light spreading properties, imparted no stickiness or no oily sensation, provided moisturizing properties, and imparted a refreshing sensation on use, as well as, at the same time, exhibited water resistance, water repellence, and perspiration resistance, exhibited good durability, and had superior stability without changing over time or without changing due to temperature.

Example 29

A hand cream comprising the components described below was prepared.

TABLE 11

| | | % by weight |
|---|---|---|
| 1 | Decamethylcyclopentasiloxane | 30 |
| 2 | Liquid paraffin | 10 |
| 3 | Amino-modified silicone gum * | 15 |
| 4 | Partially-methylated polyglycerol graft-type polysiloxane of Example 22 | 4 |
| 5 | Distearyldimethylammonium chloride | 0.8 |

TABLE 11-continued

| | | % by weight |
|---|---|---|
| 6 | Vitamin E acetate | 0.1 |
| 7 | Polyethylene glycol 4000 | 1 |
| 8 | Glycerol | 10 |
| 9 | Aluminum magnesium silicate | 1.2 |
| 10 | Preservatives | q.s. |
| 11 | Perfume | q.s. |
| 12 | Purified water | Residual quantity |

*Amino equivalent = 70,000 g/mol

Preparation Method

A: Components 1 and 3 were heated, mixed and dissolved, and Components 2, 4 to 6 and 10 were heated and added thereto.

B: Components 7 to 9 and 12 were heated and mixed.

C: The aforementioned B was gradually added to the aforementioned B, and the mixture was emulsified, followed by cooling the emulsion and adding Component 11 thereto. Thereby, a hand cream was obtained.

It can be seen that the hand cream obtained as described above exhibited light spreading properties, imparted no stickiness, imparted a refreshing sensation on use, effectively protected skin from wet work, and exhibited extremely superior temperature stability.

Example 30

A perspiration suppressor comprising the components described below was prepared.

TABLE 12

| | | % by weight |
|---|---|---|
| 1 | Octamethylcyclopentasiloxane | 30 |
| 2 | Partially-methylated polyglycerol graft-type polysiloxane of Example 22 | 1 |
| 3 | Polyoxyethylene sorbitan monooleate | 0.5 |
| 4 | Glycine salt of aluminum zirconium tetrachloride hydrate | 20 |
| 5 | Purified water | Residual quantity |

Preparation Method

A: Components 1 and 2 were mixed.

B: Component 4 was dissolved in Component 5, followed by adding Component 3 thereto.

C: The aforementioned B was gradually added to the aforementioned A under stirring to emulsify them. Thereby, a perspiration suppressor was obtained.

It can be seen that the perspiration suppressor obtained as described above exhibited light spreading properties, imparted no stickiness or no oily sensation, did not whiten much, imparted a refreshing sensation on use, and exhibited superior stability without changing over time or without changing due to temperature.

Example 31

A beautifying liquid comprising the components described below was prepared.

TABLE 13

| | | % by weight |
|---|---|---|
| 1 | Decamethylcyclopentasiloxane | 12 |
| 2 | Glyceryl triisooctanoate | 10 |
| 3 | Partially-methylated polyglycerol graft-type polysiloxane of Example 22 | 2 |
| 4 | Partially-methylated polyglycerol graft-type polysiloxane of Example 23 | 0.2 |
| 5 | Glycerol | 10 |
| 6 | Magnesium ascorbyl phosphate | 3 |
| 7 | Sodium chloride | 2 |
| 8 | Preservatives | q.s. |
| 9 | Perfume | q.s. |
| 10 | Water | Residual quantity |

Preparation Method

A: Components 1 to 4 were heated and mixed.

B: Components 5 to 8 and 10 were heated and uniformly dissolved.

C: The aforementioned B was gradually added to the aforementioned A to emulsify them, and the emulsion was cooled, followed by adding Component 9 thereto. Thereby, a beautifying liquid was obtained.

It can be seen that the beautifying liquid obtained as described above exhibited fine texture, exhibited light spreading properties, imparted no stickiness, imparted a moisturizing sensation, and exhibited extremely superior stability without changing over time or without changing due to temperature.

Example 32

A cleansing cream comprising the components described below was prepared.

TABLE 14

| | | % by weight |
|---|---|---|
| 1 | Dimethylpolysiloxane (6 cS) | 5 |
| 2 | Methylphenylpolysiloxane | 5 |
| 3 | Liquid paraffin | 8 |
| 4 | Jojoba oil | 2 |
| 5 | Partially-methylated polyglycerol graft-type polysiloxane of Example 22 | 2.5 |
| 6 | Partially-methylated polyglycerol graft-type polysiloxane of Example 23 | 0.5 |
| 7 | Dextrin fatty acid ester | 0.8 |
| 8 | Aluminum monostearate | 0.2 |
| 9 | Aluminum chloride | 1 |
| 10 | Glycerol | 10 |
| 11 | Preservatives | q.s. |
| 12 | Perfume | q.s. |
| 13 | Purified water | Residual quantity |

Preparation Method

A: Components 1 to 8 were heated and mixed.

B: Components 9 to 11 and 13 were heated and dissolved.

C: The aforementioned B was gradually added to the aforementioned A under stirring to emulsify them, and the emulsion was cooled, followed by adding Component 12 thereto. Thereby, a cleansing cream was obtained.

It can be seen that the cleansing cream obtained as described above exhibited fine texture, exhibited light spreading properties, imparted no stickiness or no oily sensation, provided moisturizing properties, and imparted a refreshing sensation on use, as well as, at the same time, exhibited increased effects of cleansing, and had superior stability without changing over time or without changing due to temperature.

Example 33

A rinsing off-type mask cosmetic comprising the components described below was prepared.

TABLE 15

| | | % by weight |
|---|---|---|
| 1 | Dimethylpolysiloxane (6 cS) | 3 |
| 2 | Partially-methylated polyglycerol graft-type polysiloxane of Example 22 | 2 |
| 3 | Kaolin | 30 |
| 4 | Carboxyvinyl polymer | 0.4 |
| 5 | 1,3-butylene glycol | 10 |
| 6 | Glycerol | 20 |
| 7 | Preservatives | q.s. |
| 8 | Perfume | q.s. |
| 9 | Purified water | Residual quantity |

Preparation Method
A: Components 1, 2 and 8 were mixed.
B: Components 4 to 7 and 9 were uniformly mixed, followed by mixing with Component 3 and stirring them.
C: The aforementioned A was added to the aforementioned B to emulsify them. Thereby, a rinsing off-type mask cosmetic in the form of a paste was obtained.

It can be seen that the rinsing off-type mask cosmetic obtained as described above exhibited light spreading properties during application, exhibited superior cleansing effects, imparted a moisturizing smooth feeling on touch without stickiness after rinsing off the mask, imparted a superior sensation during use, and also had superior stability.

Example 34

A wiping off-type cleansing composition comprising the components described below was prepared.

TABLE 16

| | | % by weight |
|---|---|---|
| 1 | Squalane | 10 |
| 2 | Liquid paraffin | 28 |
| 3 | Low-density polyethylene | 2 |
| 4 | Partially-methylated polyglycerol graft-type polysiloxane of Example 22 | 2 |
| 5 | Propylene glycol | 5 |
| 6 | Antioxidant | q.s. |
| 7 | Preservatives | q.s. |
| 8 | Perfume | q.s. |
| 9 | Purified water | Residual quantity |

Preparation Method
A: Components 1 to 4 and 6 to 8 were heated and mixed.
B: Components 5 and 9 were heated and mixed. Subsequently, the mixture was added to the aforementioned A under stirring to emulsify them. Thereby, a wiping off-type cleansing composition was obtained.

It can be seen that the wiping off-type cleansing composition obtained as described above exhibited light spreading properties during application, imparted a moisturizing sensation, and imparted a superior moisturizing sensation without stickiness after wiping off, as well as, had superior stability without changing over time or without changing due to temperature.

Example 35

A deodorant comprising the components described below was prepared.

TABLE 17

| | | % by weight |
|---|---|---|
| 1 | Decamethylpentasiloxane | 12 |
| 2 | Dimethylpolysiloxane (6 cS) | 4 |
| 3 | Partially-methylated polyglycerol graft-type polysiloxane of Example 22 | 1 |
| 4 | Propylene glycol | 31 |
| 5 | Triclosan | 0.1 |
| 6 | Glycerol | 15 |
| 7 | Preservatives | q.s. |
| 8 | Perfume | q.s. |
| 9 | Purified water | Residual quantity |

Preparation Method
A: Components 1 to 3 were mixed.
B: Component 5 was dissolved in Component 4, followed by mixing with Components 6 to 9.
C: The aforementioned B was added to the aforementioned A under vigorous stirring to emulsify them.
D: 65 parts of the aforementioned C and 35 parts of a propellant (a mixture of n-butane, isobutene, and propane) were placed in an aerosol can. Thereby, a deodorant was obtained.

It can be seen that the deodorant obtained as described above exhibited remarkably superior usability so that the deodorant did not flow even if used in increased concentration, imparted a non-sticky sensation, and exhibited durability of effects.

Example 36

A makeup remover comprising the components described below was prepared.

TABLE 18

| | | % by weight |
|---|---|---|
| 1 | Partially-methylated polyglycerol graft-type polysiloxane of Example 22 | 20 |
| 2 | Sorbitan polyoxyethylene (20) monostearate | 10 |
| 3 | Sorbitol | 10 |
| 4 | Carrageenan | 0.5 |
| 5 | Preservatives | q.s. |

TABLE 18-continued

| | | % by weight |
|---|---|---|
| 6 | Perfume | q.s. |
| 7 | Purified water | Residual quantity |

Preparation Method

A: Components 1 to 5 and 7 were added and uniformly dissolved.

B: Component 6 was added to the aforementioned A. Thereby, a makeup remover was obtained.

As a result of removing a foundation with durability by means of the makeup remover obtained as described above, good compatibility with the foundation and sebum contamination was exhibited, superior cleansing properties were exhibited, light spreading properties were exhibited, no stickiness after use was exhibited, a refreshing sensation was imparted on skin after use, and superior usability and a superior sensation in use were exhibited. In addition, it can be seen that the makeup remover also had superior stability without changing over time or without changing due to temperature.

INDUSTRIAL APPLICABILITY

The partially hydrocarbon group-blocked polyglycerol-modified polysiloxanes of the present invention are more difficult to be oxidized as compared with conventional polyether-modified polysiloxanes, are stable over time, and do not generate aldehydes which are harmful for human beings for a long period of time. Therefore, the partially hydrocarbon group-blocked (poly)glycerol-modified polysiloxanes of the present invention can be suitably used in cosmetics or the like, applied on human beings as emulsifiers without environmental pollution, as a replacement for existing polyether-modified polysiloxanes.

In addition, the partially hydrocarbon group-blocked polyglycerol-modified polysiloxanes of the present invention have reduced viscosity, as compared with conventional polyglycerol-modified polysiloxanes, and exhibit superior operation properties. For this reason, it is easy to blend in cosmetics.

The invention claimed is:

1. A partially hydrocarbon group-blocked (poly)glycerol-modified polysiloxane in which at least one terminal group is represented by formula (1), (2), or (3):

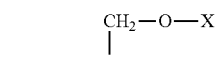 (1)

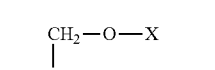 (2)

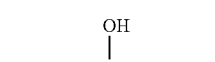 (3)

in each of the formulae, X represents a hydrogen atom or independently represents a substituted or non-substituted monovalent hydrocarbon group containing no aliphatic unsaturated bond, with not more than 20 carbon atoms;

wherein at least 15% of the Xs of the terminal groups are the hydrocarbon group, and wherein the at least one terminal group binds to a silicon atom of an organopolysiloxane via a linking group comprising a poly(glycidol) moiety.

2. The partially hydrocarbon group-blocked (poly) glycerol-modified polysiloxane according to claim 1, wherein the linking group contains a divalent group represented by general formula (4):

$$-R^1-O-(AO)_p- \quad (4)$$

wherein $R^1$ represents a substituted or non-substituted, linear or branched alkylene group having 1 to 22 carbon atoms, or a substituted or non-substituted alkylenearylene group having 6 to 22 carbon atoms;

AO independently represents an alkyleneoxy group having 1 to 4 carbon atoms, or an aryleneoxy group having 6 to 10 carbon atoms; and p represents a number ranging from 0 to 30; with the proviso that $R^1$ binds to a silicon atom, or a divalent group represented by general formula (5):

$$-R^1-COO-(AO)_p- \quad (5)$$

wherein $R^1$, AO and p are the same as described above.

3. The partially hydrocarbon group-blocked (poly) glycerol-modified polysiloxane according to claim 2, wherein the linking group further contains at least one moiety represented by formula (6), (7), (8) or (9):

 (6)

 (7)

 (8)

 (9)

wherein X is the same as described above.

4. The partially hydrocarbon group-blocked (poly)glycerol-modified polysiloxane according to claim 3, wherein the moiety is present in an amount ranging from 1 to 500 moieties in the linking group.

5. The partially hydrocarbon group-blocked (poly)glycerol-modified polysiloxane according to claim 1, wherein the partially hydrocarbon group-blocked (poly)glycerol-modified polysiloxane is represented by average unit formula (10):

$$R^2_a(R^3)_b SiO_{(4-a-b)/2} \quad (10)$$

wherein

R² represents a substituted or non-substituted monovalent hydrocarbon group containing no aliphatic unsaturated bond;

R³ represents a partially hydrocarbon group-blocked (poly)glycerol-modified group represented by —R⁴—R⁵, wherein R⁴ represents the linking group; and R⁵ represents the terminal group; and $1.0 \leq a \leq 2.5$, and $0.001 \leq b \leq 1.5$.

6. A method for producing a partially hydrocarbon group-blocked (poly)glycerol-modified polysiloxane of claim 1, the method comprising reacting an organohydrogenpolysiloxane and a partially hydrocarbon group-blocked (poly)glycerol in which at least one terminal group represented by formula (1), (2) or (3):

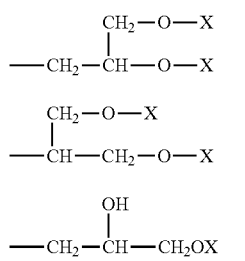

in each of the formulae, X represents a hydrogen atom or independently represents a substituted or non-substituted monovalent hydrocarbon group containing no aliphatic unsaturated bond, with not more than 20 carbon atoms; and at least 15% of the Xs of the terminal groups are the hydrocarbon group, and wherein the at least one terminal group binds to an aliphatic unsaturated hydrocarbon group via a linking group comprising a poly(glycidol) moiety, in the presence of an addition reaction catalyst.

7. The method for producing a partially hydrocarbon group-blocked (poly)glycerol-modified polysiloxane according to claim 6, wherein the linking group contains a divalent group represented by general formula (4'):

wherein

R⁶ represents a substituted or non-substituted, linear or branched alkylene group having 1 to 20 carbon atoms, or a substituted or non-substituted alkylenearylene group having 6 to 20 carbon atoms;

AO independently represents an alkyleneoxy group having 1 to 4 carbon atoms, or an aryleneoxy group having 6 to 10 carbon atoms; and p represents a number ranging from 0 to 30; with the proviso that R⁶ binds to the aliphatic unsaturated hydrocarbon group, or a divalent group represented by general formula (5'):

wherein

R⁶, AO, and p are the same as described above.

8. The method for producing a partially hydrocarbon group-blocked (poly)glycerol-modified polysiloxane according to claim 7, wherein the linking group further contains at least one moiety represented by formula (6), (7), (8) or (9):

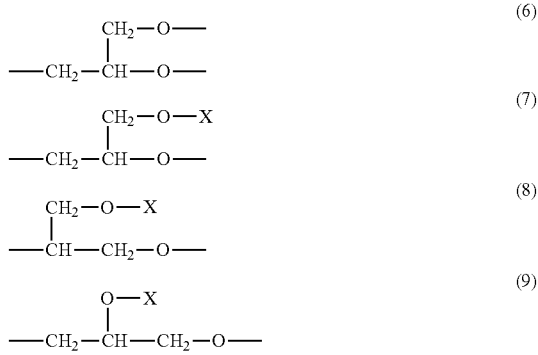

wherein X is the same as described above.

9. The method for producing a partially hydrocarbon group-blocked (poly) glycerol-modified polysiloxane according to claim 6, wherein the organohydrogenpolysiloxane is represented by average unit formula (II):

wherein

R² represents a substituted or non-substituted monovalent hydrocarbon group containing no aliphatic unsaturated bond; and $1.0 \leq a \leq 2.5$, and $0.001 \leq b \leq 1.5$.

10. The method for producing a partially hydrocarbon group-blocked (poly)glycerol-modified polysiloxane according to claim 6, wherein the aliphatic unsaturated hydrocarbon group is a vinyl group or an allyl group.

11. A cosmetic comprising the partially hydrocarbon group-blocked (poly)glycerol-modified polysiloxane as recited in claim 1.

* * * * *